US007789230B2

(12) United States Patent  (10) Patent No.: US 7,789,230 B2
Klein  (45) Date of Patent: Sep. 7, 2010

(54) METHOD AND APPARATUS FOR COLLECTING SHARPS

(75) Inventor: Ronald T. Klein, Island Lake, IL (US)

(73) Assignee: Covidien AG (CH)

( * ) Notice: Subject to any disclaimer, the term of this patent is extended or adjusted under 35 U.S.C. 154(b) by 651 days.

(21) Appl. No.: 11/235,921

(22) Filed: Sep. 27, 2005

(65) Prior Publication Data

US 2007/0068831 A1    Mar. 29, 2007

(51) Int. Cl.
B65D 83/10    (2006.01)
(52) U.S. Cl. .................................. 206/366; 206/370
(58) Field of Classification Search ......... 206/363–370; 220/908, 910; 604/110
See application file for complete search history.

(56) References Cited

U.S. PATENT DOCUMENTS

| 2,576,019 | A | 11/1951 | Kisselle |
| 2,623,529 | A | 12/1952 | Soule |
| 2,695,619 | A | 11/1954 | Soule |
| 4,453,648 | A | 6/1984 | Harris et al. |
| 4,565,311 | A | 1/1986 | Pugliese et al. |
| 4,580,688 | A | 4/1986 | Harris et al. |
| 4,618,103 | A | 10/1986 | Wilson et al. |
| 4,715,498 | A | 12/1987 | Hanifl |
| 4,736,860 | A | 4/1988 | Bemis |
| 4,779,728 | A | 10/1988 | Hanifl et al. |
| 4,804,090 | A | 2/1989 | Schuh et al. |
| 4,809,850 | A | 3/1989 | Laible et al. |
| 4,828,107 | A | 5/1989 | Spencer |
| 4,842,138 | A * | 6/1989 | Sandel et al. ............... 206/370 |
| 4,869,366 | A | 9/1989 | Bruno |
| D304,493 | S | 11/1989 | Bemis |
| 4,890,733 | A | 1/1990 | Anderson |
| 4,903,832 | A | 2/1990 | Stewart |
| 4,913,309 | A | 4/1990 | Fink |
| 4,955,477 | A | 9/1990 | Bruno |
| RE33,413 | E | 10/1990 | Hanifl |
| 5,076,429 | A | 12/1991 | Patrick et al. |
| 5,080,251 | A | 1/1992 | Noack |
| 5,097,950 | A | 3/1992 | Weiss et al. |
| 5,103,997 | A | 4/1992 | Noack |
| 5,137,260 | A | 8/1992 | Pehr |
| 5,152,394 | A | 10/1992 | Hughes |
| 5,154,345 | A | 10/1992 | Shillington |

(Continued)

FOREIGN PATENT DOCUMENTS

EP    1 447 109    8/2004

OTHER PUBLICATIONS

International Search Report corresponding to International Application No. PCT/US2006/036642 dated Dec. 29, 2006.

*Primary Examiner*—Luan K Bui
(74) *Attorney, Agent, or Firm*—Lisa E. Winsor, Esq.

(57) ABSTRACT

A container for collecting sharps includes an opening adapted to receive sharps in a substantially vertical orientation, and an interior region for storing sharps received through the opening. The container includes a means for reorienting the sharps into an arrangement in which the sharps lie substantially parallel to one another within the interior region of the container. A method for configuring a sharps collection container includes the step of positioning a contoured surface of a guide element beneath an opening of the container to reorient sharps that are deposited through the opening into an arrangement in which the sharps are stored substantially parallel to one another in the container.

24 Claims, 19 Drawing Sheets

U.S. PATENT DOCUMENTS

| | | | |
|---|---|---|---|
| 5,178,322 A | 1/1993 | Shillington | |
| 5,217,688 A | 6/1993 | Von Lersner | |
| 5,240,108 A | 8/1993 | Tonna | |
| 5,273,161 A | 12/1993 | Sagstetter | |
| 5,346,086 A | 9/1994 | Harris | |
| 5,351,381 A | 10/1994 | Case | |
| 5,387,735 A * | 2/1995 | Ponsi et al. | 206/366 |
| 5,409,112 A | 4/1995 | Sagstetter | |
| 5,413,243 A | 5/1995 | Bemis et al. | |
| 5,415,315 A | 5/1995 | Ramirez | |
| 5,419,435 A * | 5/1995 | Perzan et al. | 206/366 |
| 5,423,450 A | 6/1995 | Shillington et al. | |
| 5,435,484 A | 7/1995 | Carlson | |
| 5,469,964 A | 11/1995 | Bailey | |
| 5,494,158 A | 2/1996 | Erickson | |
| 5,494,186 A | 2/1996 | Marsh | |
| 5,560,512 A * | 10/1996 | Hahn | 220/908 |
| 5,570,783 A | 11/1996 | Thorne et al. | |
| 5,603,404 A | 2/1997 | Nazare et al. | |
| 5,605,245 A | 2/1997 | Bemis et al. | |
| 5,647,502 A | 7/1997 | Marsh | |
| 5,740,909 A | 4/1998 | Nazare et al. | |
| 5,848,692 A | 12/1998 | Thorne et al. | |
| 5,887,807 A | 3/1999 | Beinecke | |
| 5,918,739 A | 7/1999 | Bilof et al. | |
| 5,947,285 A * | 9/1999 | Gaba et al. | 206/366 |
| D414,864 S | 10/1999 | Gaba et al. | |
| 5,967,317 A | 10/1999 | Wright | |
| 5,979,275 A | 11/1999 | Waluda | |
| D421,122 S | 2/2000 | Gaba et al. | |
| D438,964 S | 3/2001 | Gaba et al. | |
| 6,250,465 B1 | 6/2001 | Daniels et al. | |
| 6,253,916 B1 | 7/2001 | Bickel | |
| 6,283,909 B1 | 9/2001 | Sharp | |
| 6,561,352 B2 | 5/2003 | Sherman et al. | |
| 6,568,614 B2 | 5/2003 | Chen et al. | |
| 6,685,017 B2 | 2/2004 | Erickson | |
| 6,792,662 B2 | 9/2004 | Samuel | |
| 6,923,318 B1 | 8/2005 | Erickson et al. | |
| 2003/0132129 A1 | 7/2003 | Erickson | |
| 2003/0168367 A1* | 9/2003 | Pike | 206/366 |
| 2003/0213714 A1 | 11/2003 | Moats et al. | |
| 2004/0134817 A1 | 7/2004 | Bickel et al. | |
| 2005/0236289 A1 | 10/2005 | Tanaka et al. | |
| 2005/0269226 A1 | 12/2005 | Erickson et al. | |
| 2005/0269227 A1 | 12/2005 | Erickson et al. | |

* cited by examiner

METHOD AND APPARATUS FOR COLLECTING SHARPS

FIELD OF THE INVENTION

The present invention relates generally to containers for collecting and storing sharps, and particularly to storage containers that reorient sharps as they are collected so that the sharps accumulate in a consolidated arrangement.

BACKGROUND OF THE INVENTION

A variety of containers have been developed for the collection and storage of needle syringes and other sharps. A primary function of the containers is to provide a rigid enclosure that protects individuals from becoming injured by an exposed sharps. This function is especially significant in the handling of used sharps during disposal. Used sharps that are not properly contained pose a risk of serious injury to personnel who handle the used sharps. Accidental contact with a used needle can result in the transmission of various pathogens, including human immunodeficiency virus (HIV). In view of the risks associated with exposed sharps, sharps containers provide a safe way to store sharps during transport and disposal.

A frequent problem encountered with sharps containers is limited storage capacity. Many sharps, including syringes and blood collection devices, have long and narrow geometries. When a number of elongated sharps are dropped into a sharps container, the sharps tend to accumulate in a random and disorganized manner, with many sharps piling up in an uneven arrangement. In some cases, the sharps may be propped up on one another in a criss-cross pattern, creating relatively large void spaces between the sharps. The void spaces can occupy a significant amount of the volume of the container, reducing the storage capacity of the container and increasing the frequency in which the container must be emptied or replaced. It is therefore desirable to minimize the accumulation of void spaces between sharps as sharps are collected in the containers.

SUMMARY OF THE INVENTION

The foregoing concerns are addressed to a large degree by a sharps collection container in accordance with the present invention. According to one embodiment, the sharps container includes one or more openings adapted to receive sharps in a substantially vertical orientation, and an interior region for collecting sharps. In addition, the container includes a means for reorienting the sharps into an arrangement in which the sharps lie substantially parallel to one another within the interior region of the container.

In another embodiment of the invention, a sharps collection container includes an opening adapted to receive sharps in a substantially vertical orientation, and an interior region located beneath the opening for collecting sharps that are dropped into the opening. A carrier is mounted to the container for movement between a sharps-receiving position, in which the carrier receives and retains sharps in a substantially vertical position, and a sharps-releasing position, in which the carrier releases the sharps into the interior region of the container in a substantially horizontal position.

In another embodiment of the invention, a sharps collection container includes an opening, an interior region located beneath the opening for collecting sharps received through the opening, and a ramp extending downwardly from the opening and toward the interior region of the container. The ramp is generally aligned beneath the opening to deflect and reorient sharps that are inserted into the opening.

In another embodiment of the invention, a sharps collection container includes an opening, an interior region located beneath the opening for collecting sharps received through the opening, and a substantially planar platform extending beneath the opening to deflect and reorient sharps that are inserted into the opening.

In another embodiment of the invention, a sharps collection container includes an opening adapted to receive sharps in a substantially vertical orientation, an interior region located beneath the opening for collecting sharps received through the opening, and a deflector positioned to guide sharps between the opening and the interior region. The deflector may include one or more ramp surfaces arranged beneath the opening and configured to reorient the sharps from the substantially vertical orientation to an arrangement in which the sharps are positioned in the interior region substantially parallel to one another.

In another embodiment of the invention, a sharps collection container includes an opening adapted to receive sharps in a substantially vertical orientation, an interior region located beneath the opening, and a cowl extending between the opening and the interior region. The cowl is positioned beneath the opening to guide the sharps received through the opening toward the interior region of the container in an arrangement in which the sharps are positioned substantially parallel to one another.

In another embodiment of the invention, a method for configuring a sharps collection container includes the step of positioning a contoured surface of a guide element beneath an opening of the container to reorient sharps that are deposited through the opening from a substantially vertical orientation into an arrangement in which the sharps are substantially parallel to one another.

In another embodiment of the invention, a method for configuring a sharps collection container includes the step of providing a container having an opening for receiving sharps, and the step of positioning a contoured surface of a guide element beneath the opening of the container to reorient sharps that are deposited through the opening from a substantially vertical orientation into an arrangement in which the sharps are substantially parallel to one another.

In another embodiment of the invention, a method for configuring a sharps collection container includes the step of forming a ramp extending downwardly from a position proximal an opening in the container and toward the interior region of the container to deflect sharps that are received through the opening and to reorient sharps that are deposited through the opening into an arrangement in which the sharps are substantially parallel to one another.

In another embodiment of the invention, a method for configuring a sharps collection container includes the step of forming a ramp extending downwardly from a position proximal an opening in the container and toward the interior region of the container to deflect sharps that are received through the opening and to reorient sharps that are deposited through the opening, and the step of forming a substantially planar platform supported on a pivot in the container, the platform extending beneath the opening to deflect and reorient sharps that are inserted into the opening.

In another embodiment of the invention, a method for configuring a sharps collection container includes the step of forming a first ramp and a second ramp beneath an opening in the container, where the second ramp is positioned in a symmetrical arrangement with the first ramp to reorient sharps that are deposited through the opening from a substantially vertical orientation into an arrangement in which the sharps are substantially parallel to one another.

In another embodiment of the invention, a method for configuring a sharps collection container includes the step of positioning a cowl beneath an opening of the container to reorient sharps that are inserted into the opening into an arrangement in which the sharps are substantially parallel to one another.

BRIEF DESCRIPTION OF THE DRAWINGS

The foregoing summary as well as the following description will be better understood when read in conjunction with the figures in which.

DETAILED DESCRIPTION OF THE INVENTION

Figure 1:
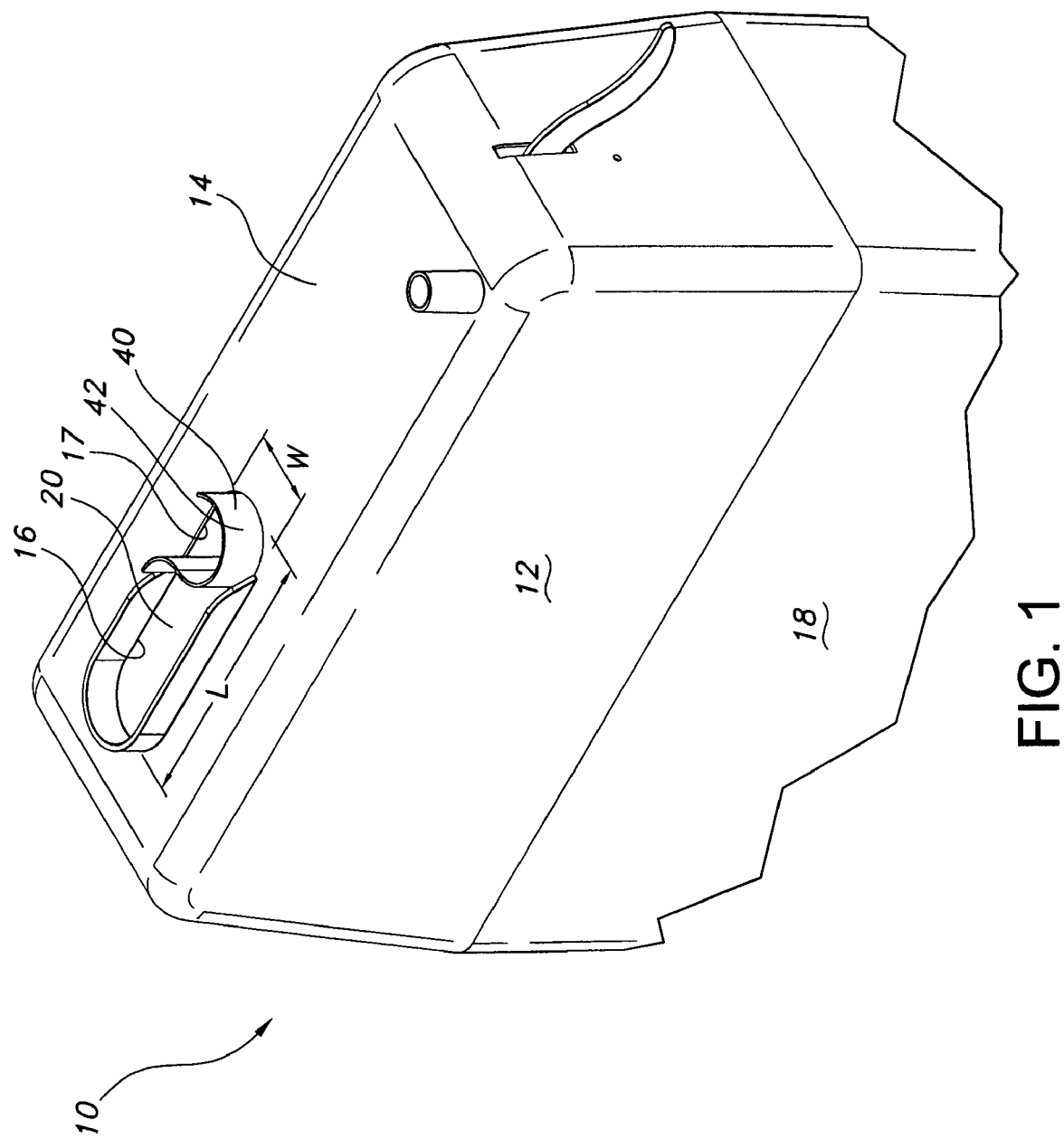
FIG. 1 is a truncated perspective view of a sharps collection container in accordance with a first embodiment of the invention.

Although the invention is illustrated and described herein with reference to specific embodiments, the invention is not intended to be limited to the details shown. Rather, various modifications may be made in the details within the scope and range of equivalents of the claims and without departing from the invention.

Referring to the drawing figures in general, a number of container embodiments are illustrated in accordance with the present invention. The containers have openings for receiving sharps in a substantially vertical orientation, and interior areas for storing sharps that are deposited through the openings of the containers. Sharps that are inserted through the openings of the containers are reoriented by one or more guide elements so that the sharps are deposited into the container in a substantially parallel or "stacked" arrangement. In this arrangement, the sharps accumulate in a more consolidated manner, reducing the accumulation and/or size of voids formed between the sharps. The improved consolidation of sharps increases the storage capacity of the sharps container and decreases the number of containers that are consumed over time.

Referring now to FIGS. 1-5, a first embodiment of a sharps collection container 10 is shown in accordance with the present invention. The container 10 includes a cover portion 12 and a bottom portion or receptacle 18 positioned beneath the cover portion. The cover portion 12 has an elongated opening 16 for receiving sharps. The receptacle 18 forms an interior storage area or region 20 beneath the opening 16 for collecting sharps that are deposited through the opening in the cover 12. A guide mechanism 30 conveys sharps from the opening 16 to the interior region 20 of the receptacle 18. The guide mechanism 30 reorients the sharps so that the sharps are more or less aligned with one another and accumulate in the interior region 20 of the receptacle 18 in a more consolidated arrangement.

The cover portion 12 forms a hollow enclosure having a top face 14. The opening 16 extends through the top face 14, forming a passage into the interior of the cover portion and a clearance space for movement of a carrier 40 (discussed below) between a sharps-receiving position and a sharps-releasing position. The dimensions of the opening 16 (in cooperation with the carrier 40 discussed below) permit the insertion of sharps through the cover 12 in an endwise manner, but inhibit or prevent insertion of sharps in a lengthwise manner. In particular, the opening 16 has a width (labeled "W" in FIG. 1) that is slightly larger than the width of most sharps, and a length (marked "L" in FIG. 1) that is smaller than the length of most sharps. This configuration encourages users to hold sharps in a substantially vertical orientation, and more particularly to hold sharps with the pointed end facing more or less straight down. This decreases the risk of injury to others who may be in the vicinity of the user.

Figure 2:
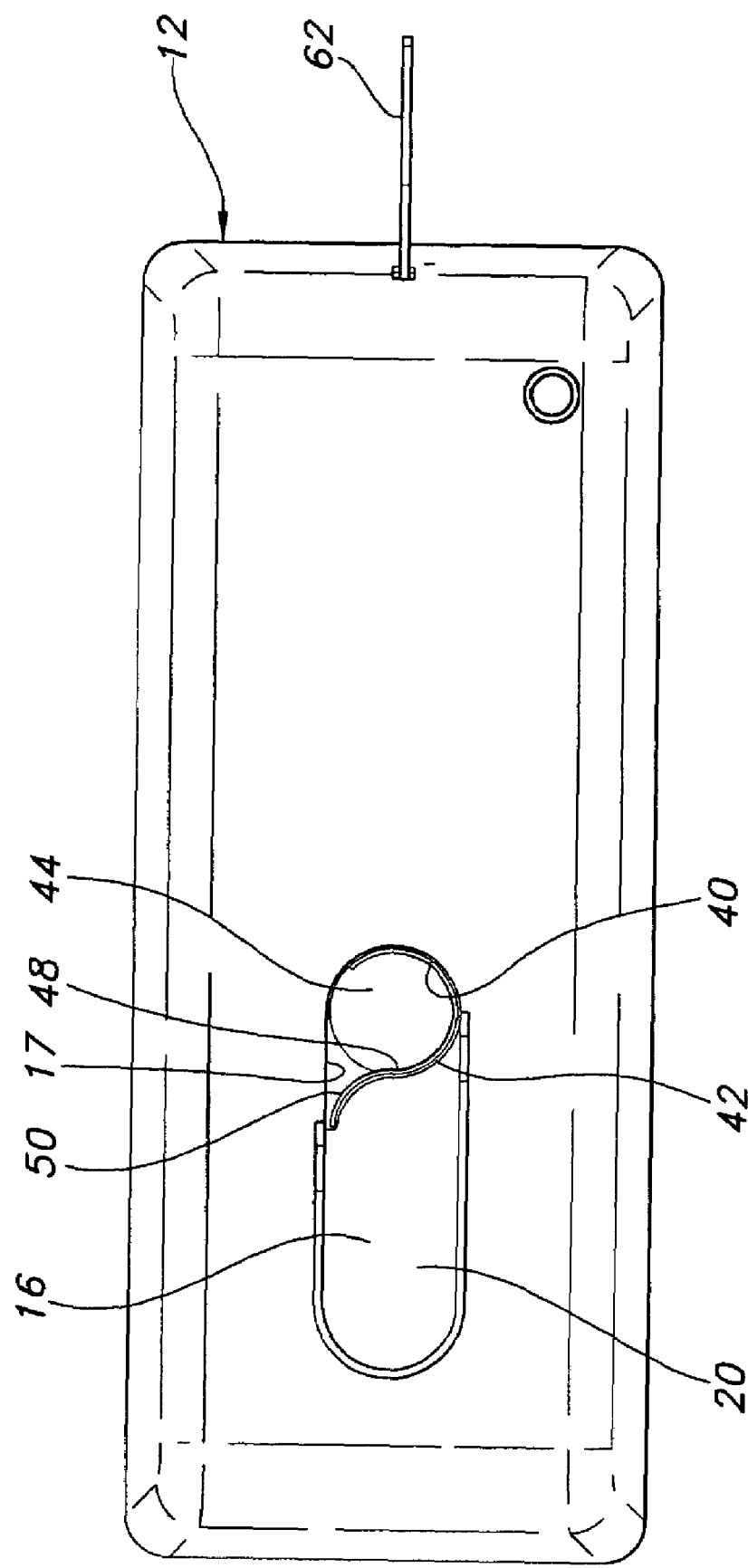
FIG. 2 is a top view of a cover on the sharps collection container of FIG. 1.
Figure 3:
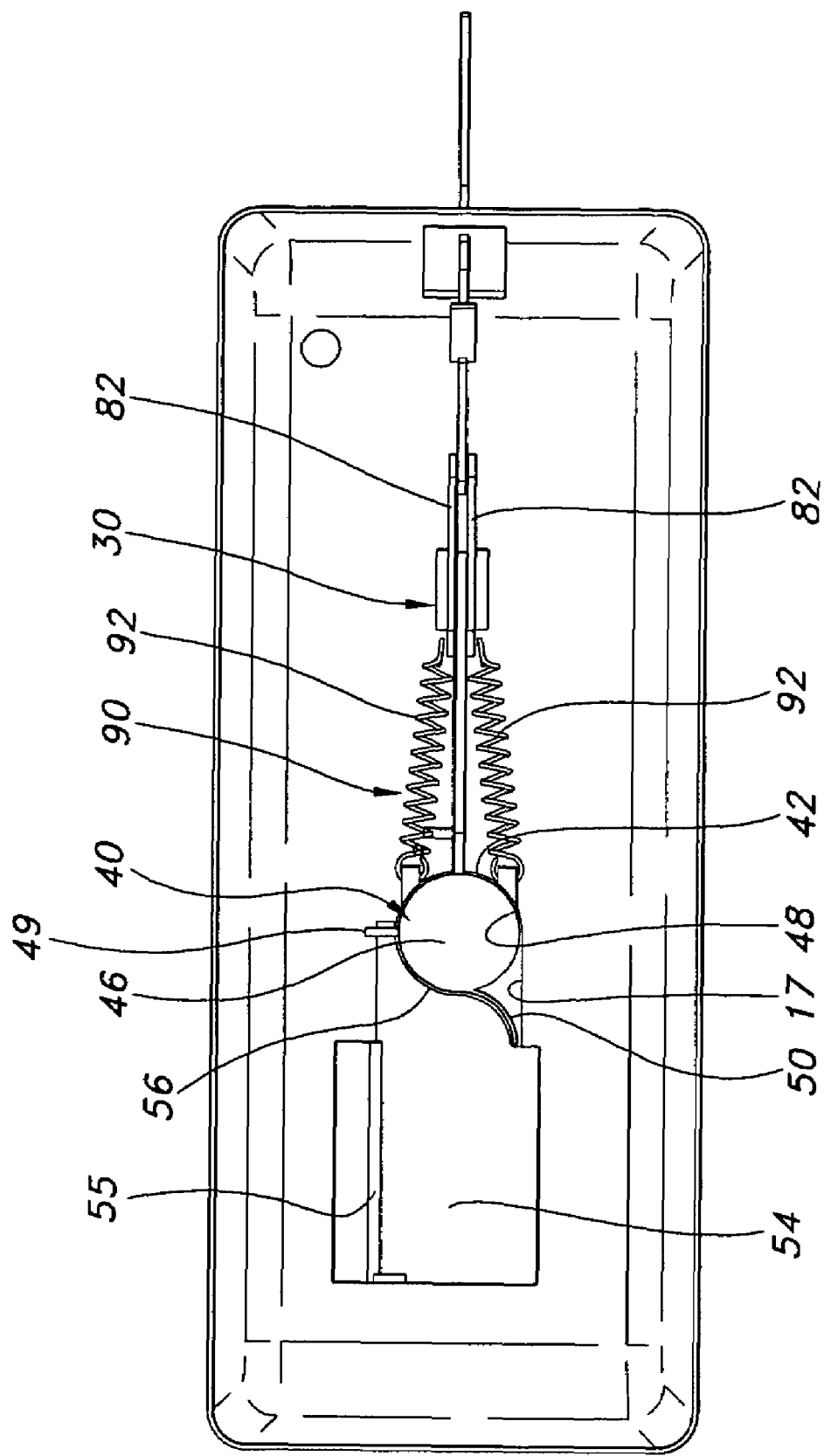
FIG. 3 is a bottom view of the cover on the sharps collection container of FIG. 1.

The guide mechanism 30 includes a carrier 40 for receiving sharps that are to be inserted through the opening 16. The carrier 40 may include a wide variety of geometrical configurations for receiving sharps. Referring to FIGS. 2 and 3, for example, the carrier 40 optionally includes a generally cylindrical tubular compartment 42 having an open end 44 for receiving sharps, and a closed end 46 for holding the sharps in the compartment. The open end 44 of the tubular compartment preferably projects through the opening 16 and above the top face 14 of the cover 12, so that the carrier can be easily identified upon viewing the top portion of the container. The tubular compartment 42 need not project out of the opening, however, and the guide mechanism 30 can function equally well with the tubular compartment recessed beneath the top face 14.

The dimensions of the carrier 40 may be selected to accommodate a variety of sharps devices, including but not limited to syringes, blood collection devices and vial injectors. The tubular compartment 42 of the carrier 40 has a length sufficient to receive all or a substantial portion of the length of the sharps. In addition, the open end 44 has a cross sectional area that is larger than the cross-sectional area of the sharps, such that the sharps can be inserted into the carrier 40 in an endwise manner.

Figure 4:
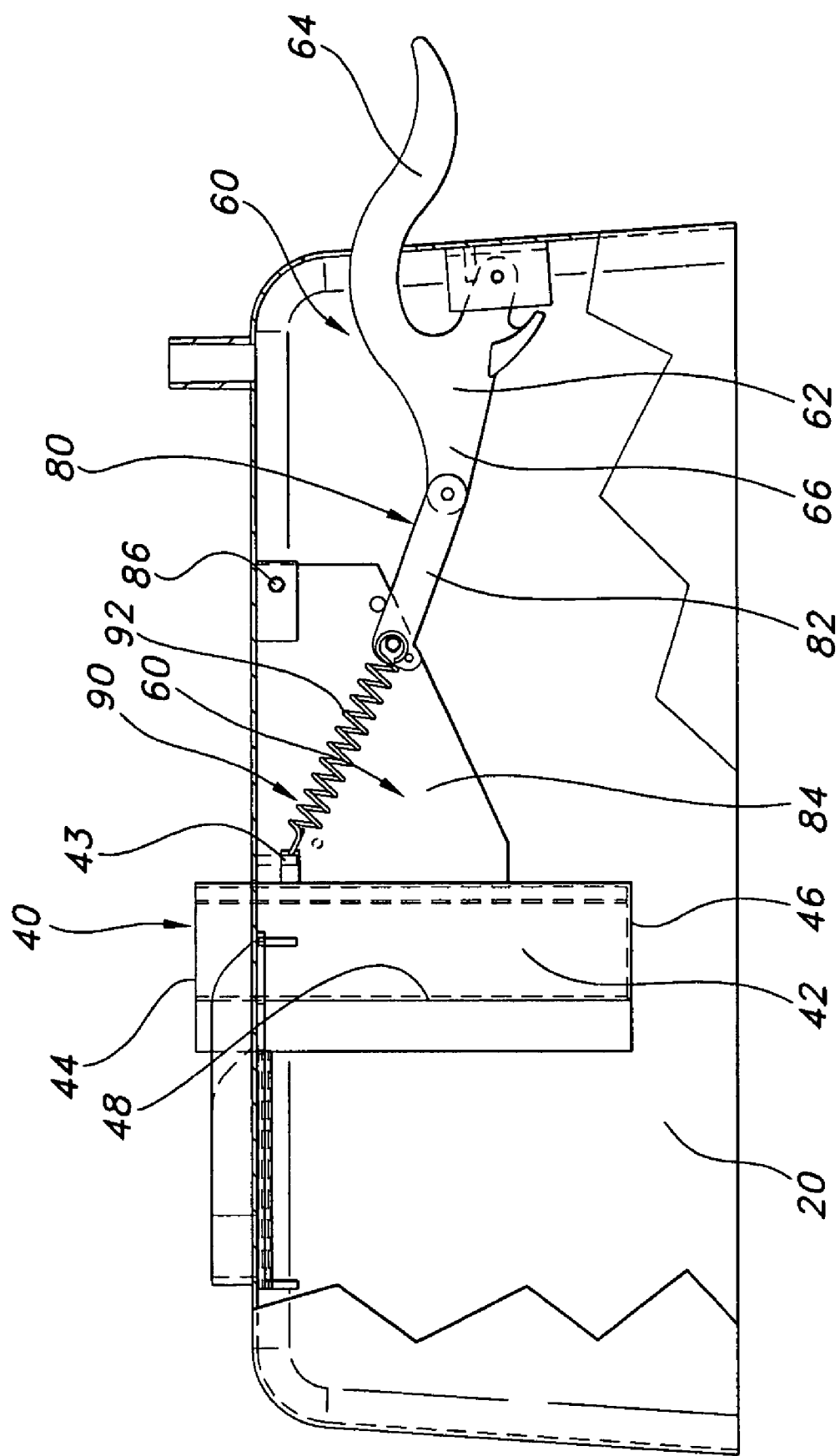
FIG. 4 is a front view of the cover on the sharps collection container of FIG. 1, with a portion of the cover broken away to illustrate internal components arranged in a first position.
Figure 5:
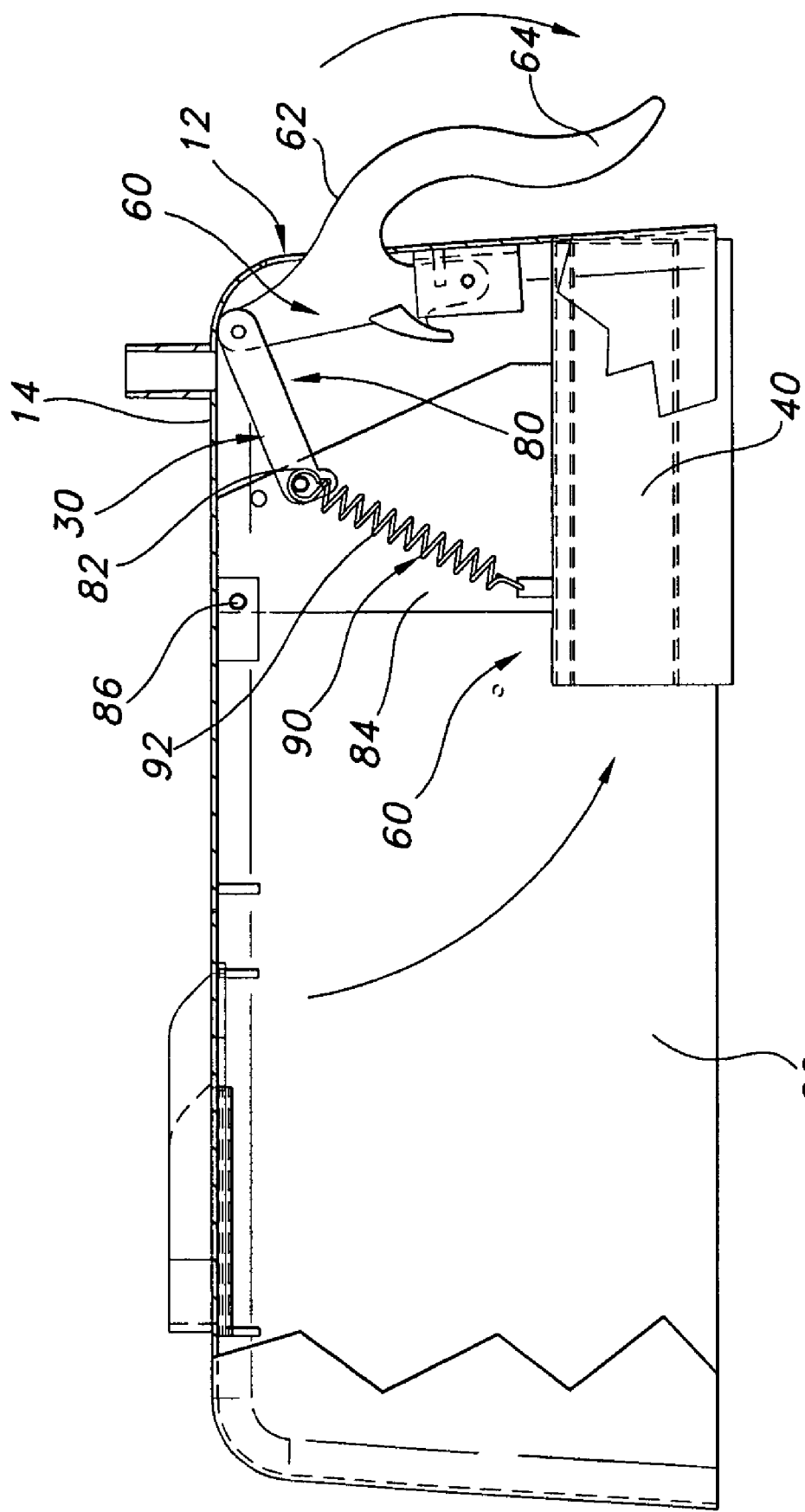
FIG. 5 is a front view of the cover of the sharps collection container of FIG. 1, with a portion of the cover broken away to illustrate internal components arranged in a second position.

The carrier 40 is movable within the container 10 to convey the sharps from the opening 16 of the container into the interior region 20 of the container. The carrier 40 may be mounted in a variety of movable arrangements to reorient the sharps. Referring to FIGS. 4 and 5, for example, the carrier 40 is pivotally mounted in the container. In particular, the carrier 40 is pivotal between a sharps-receiving position, as illustrated in FIG. 4, and a sharps-releasing position, as shown in FIG. 5. In the sharps-receiving position, the longitudinal axis of the tubular compartment 42 is in a substantially vertical or upright orientation, with the open end 44 exposed through or above the opening 16 in the top face 14 of the cover 12, and the closed end 46 positioned beneath the top face of the cover. In this orientation, the carrier 40 can easily receive a sharps being held in a substantially vertical position, and hold the sharps in a substantially vertical orientation. In the sharps-releasing position, the carrier 40 is pivoted beneath the top face 14 of the cover 12, with the longitudinal axis of the tubular compartment 42 lying in a substantially horizontal orientation. In this position, the sharps is reoriented into a substantially horizontal orientation.

Although the carrier 40 is optionally pivotal between a vertical sharps-receiving position, as illustrated in FIG. 4, and a horizontal sharps-releasing position, as shown in FIG. 5, near vertical and horizontal positions are contemplated as well. For example, any sharps-receiving orientation suitable to receive a sharps as it is deposited in the container is contemplated. Similarly, any sharps-releasing orientation suitable to release a sharps as it is transferred to the interior region of the container is also contemplated.

Referring to FIG. 5, the carrier 40 may extend slightly below the bottom of the cover 12 in the sharps-releasing position. Since the carrier 40 extends into the receptacle 18, a small amount of clearance space should be maintained in the receptacle as the receptacle fills with sharps, so that the carrier can freely pivot into the receptacle without being blocked by sharps that accumulate in the receptacle. It may be desirable to limit the extent to which the components of the guide mechanism 30 extend beneath the cover 12, in the interest of eliminating the need to reserve a certain amount of clearance space in the receptacle. Clearance space takes away from the storage capacity in the receptacle. To this end, the height of the cover 12 may be increased, the dimensions of the guide mechanism 30 decreased, or both, so that the carrier 40 remains above the top rim of the receptacle or above a fill level of the container.

The carrier 40 is movable between the sharps-receiving position and the sharps-releasing position by an actuator 60. The actuator 60 may utilize a variety of mechanical or electrical components for moving the carrier 40. Referring to FIGS. 4 and 5, for example, the actuator 60 includes a lever 62 that extends through a wall of the container and connects to the carrier 40 by a linkage 80. The lever 62 has an elongated handle section 64 that projects outside the cover 12, and a linkage section 66 that connects with the linkage 80. The linkage 80 includes a pair of pivot arms 82. The pivot arms 82 are, in turn, pivotally connected to a back plate 84 that extends from the tubular compartment 42. The back plate 84 is pivotally mounted to a top portion of the cover 12 by a pin 86. In this arrangement, the lever 62, linkage 80 and back plate 84 are cooperatively engaged to convert linear displacement of the handle 64 into pivotal displacement of the carrier 40.

The handle 64 is displaceable in a generally vertical motion in response to force applied manually to the handle. The handle 64 is movable between a raised position, which positions the carrier 40 in the sharps-receiving position, and a lowered position, which positions the carrier in the sharps-releasing position. In many cases, it will be desirable to maintain the carrier 40 in the sharps-receiving position, so that the container 10 is always ready to receive sharps. Such an arrangement eliminates the step of operating the handle prior to placing the sharps into the carrier 40. In view of this desire, the container 10 preferably includes a biasing means that biases the carrier 40 toward the sharps-receiving position. A variety of biasing means suitable for this purpose may be used, including but not limited to one or more springs or counterweights. Referring to FIG. 4, for example, a biasing means 90 includes a pair of tension springs 92 that are attached between the tubular compartment 42 and the linkage 80. Each tension spring 92 has a first end, which is attached to a hook 43 on a side portion of the tubular compartment 42, and a second end, which is attached to the linkage 80. The distance between the hooks 43 and the linkage 80 is greater when the carrier 40 is in the sharps-releasing position than when the carrier is in the sharps-receiving position. In addition, the distance between the hooks 43 and the linkage 80 when the carrier 40 is in the sharps-releasing position exceeds the relaxed length of the tension springs 92. As such, the springs 92 are placed under tension and acquire stored energy in response to displacement of the carrier 40 from the sharps-receiving position to the sharps-releasing position. As explained below in connection with the operation of the container 10, the stored energy of the tension springs 92 returns the carrier to the sharps-receiving position when the handle 64 of the actuator 60 is released by the user.

The tubular compartment 42 forms a partially open cylinder, with one portion of the wall defining a longitudinal slot 48. The slot 48 has a width that is larger than the width of the sharps in the tubular compartment 42. In this arrangement, the sharps can be released from the tubular compartment 42 through the slot 48 when the carrier is pivoted to the sharps-releasing position. When the carrier 40 is disposed in the sharps-receiving position, the slot 48 is obstructed by a side edge 17 of the opening 16. The wall of the tubular compartment 42 and the side edge 17 of opening 16 effectively trap the sharps within the compartment and prevent the sharps from slipping through the slot 48. When the carrier 40 is disposed in the sharps-releasing position, the slot 48 is pivoted out of alignment with the side edge 17 of opening 16 to an unobstructed position inside the cover 12.

As noted above, sharps that are placed in the carrier 40 are oriented in, or at least toward, a substantially horizontal orientation when the carrier is moved to the sharps-releasing position. In the sharps-releasing position, the longitudinal slot 48 opens out into the interior of the container 10 to permit the sharps to be released from the tubular compartment 42 and into the interior region 20 of the container 10. The slot 48 preferably lies adjacent to the lowest point on the circumference of the tubular compartment 42 when the carrier is in the sharps-releasing position. As will be explained below, this positioning of the slot allows sharps to drop out of the compartment in response to gravity and in response to the downward momentum of the sharps.

The carrier 40 may be configured so that sharps are released from the compartment 42 by free-fall or by rolling out of the compartment. Referring to FIGS. 2 and 3, the carrier 40 includes a contoured surface that allows sharps to roll out of (or be deflected out of) the tubular compartment 42 and drop into the interior region 20 of the container 10. In particular, the carrier 40 includes a contoured extension or ramp 50 that forms a gradually sloped surface. The contoured ramp 50 extends outwardly from the tubular compartment 42 along one side of the slot. When the carrier is pivoted to the sharps-releasing position, the contoured ramp 50 extends outwardly beneath the tubular compartment 42. The slot 48 extends along one side of the compartment 42 and is oriented to allow the sharps to roll out of the carrier 40 when the carrier moves to or toward the sharps-releasing position (i.e., as the carrier moves to or toward the horizontal position). The ramp 50 preferably extends along the entire length of the tubular compartment 42 to maximize the contact area between the ramp and the sharps. In this arrangement, the ramp 50 contacts all or a substantial portion of the length of the sharps to keep the sharps relatively stable until the point of release. As will be explained below in connection with the operation of the carrier 40, the relative stability of the sharps prior to the point of release facilitates a smooth release so that the sharps remains substantially horizontal or at least more horizontal as it drops into the interior region 20 of the container 10.

As can be seen in FIGS. 1 and 2, the carrier 40 occupies one end of the elongated opening 16 when the carrier is in the sharps-receiving position. It may be desirable to temporarily block or close the remaining unoccupied portion of the opening 16 when the carrier is in the sharps-receiving position to prevent or inhibit, for example, the dropping of objects directly through the unoccupied portion of the opening. Blocking or closing the door also prevents sharps from spilling out of the opening 16 in the event that the container is inadvertently tipped over.

To this end, the container 10 optionally includes a door that partially or completely blocks the unoccupied portion of the opening 16 when the carrier 40 is in the sharps-receiving position. Referring to FIG. 3, the container 10 includes a trap door 54 that extends beneath the unoccupied portion of the opening 16. The trap door 54 is pivotally supported on one side by a hinge 55 that permits the trap door to be moved between a closed position and an open position. In the closed position, which is shown in FIG. 3, the trap door covers the unoccupied portion of opening 16. In the open position, the trap door 54 is moved downwardly into the cover portion 12, so that the carrier 40 can pass through the opening. The trap door 54 includes a curved edge 56 that conforms to the shape and curvature of the tubular compartment 42 and ramp 50. The carrier 40 includes a guide hook 49 that supports the underside of the trap door 54 along the curved edge 56. When the carrier 40 is pivoted from the sharps-receiving position toward the sharps-releasing position, the guide hook 49 pivots downwardly with the carrier, allowing the trap door 54 to drop downwardly into the cover 12. The guide hook 49 glides along the curved edge 56 as the trap door 54 descends and remains in a supporting engagement with the curved edge of the trap door. When the trap door 54 reaches the open position, the guide hook 49 remains underneath the trap door. When the carrier 40 is moved back to the sharps-receiving position, the guide hook 49 imparts an upward force on the underside of the trap door 54 and pushes the trap door back to the closed position.

Figure 6:
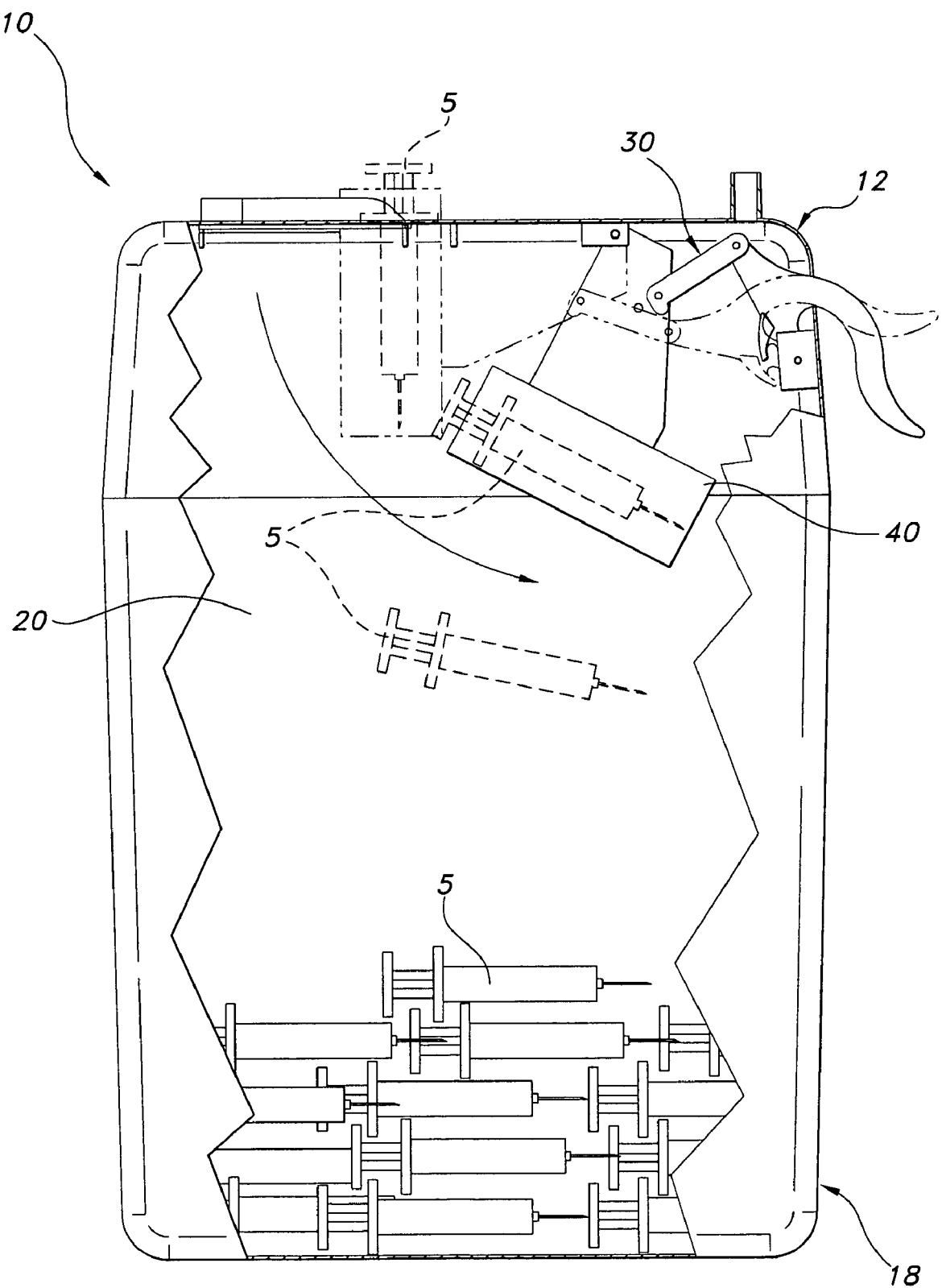
FIG. 6 is a front view of the sharps collection container of FIG. 1, with a portion of the container broken away.

Referring now to FIGS. 4-6, the operation of the container 10 will now be described. After the cover 12 is properly attached to the receptacle 18, a sharps 5 is held above the carrier 40 in a substantially vertical position. If the container 10 includes a biasing element 90, the carrier 40 will already be set in the sharps-receiving position, and the sharps 5 can be placed into the carrier. In the event that the carrier is not set in the sharps-receiving position, the handle portion 64 of the actuator 60 is raised. As the handle 64 is raised, the torque applied to the handle is transferred through the pivot arms 82 and back plate 84 to pivot the carrier 40 to the sharps-receiving position.

The sharps 5 is positioned over the opening 44 with the pointed end preferably aimed downwardly into the tubular compartment 42 of the carrier 40. Once aligned, the sharps is inserted into the opening until the pointed end contacts the bottom wall 46 of the tubular compartment 42. Alternatively, the user can drop the sharps 5 into the tubular compartment 42 by holding the sharps above the tubular compartment within a small distance from the opening and releasing the grip on the sharps. The sharps 5 will rest inside the tubular compartment in a substantially vertical orientation.

Once the sharps 5 is resting in the tubular compartment 42, the actuator 60 is operated to pivot the carrier from the sharps-receiving position to the sharps-releasing position. The handle 64 of the actuator 60 is pressed downwardly by applying a downward force on the handle. In the event that the tension springs 92 are present, the downward force must exceed the combined tensile resistance of the tension springs 92 and any frictional resistance introduced by the components between the actuator 60 and carrier 40. When the downward force applied to the handle 64 exceeds the resistances present in the components, the carrier 40 will pivot in a substantially vertical plane through an angle of up to approximately 90 degrees or more until the carrier reaches the sharps-releasing position.

As the carrier 40 pivots to the sharps-releasing position, the top end of the tubular compartment 42 passes through the opening 16 in the top face 14 of the container. In most cases, the length of the sharps 5 will be longer than the depth of the compartment, so that a portion of the length of the sharps will project above the compartment and the opening 16. The elongated shape of the opening 16 provides sufficient clearance to accommodate the portion of the sharps that protrudes above the top face 14 of the cover 12.

As the carrier 40 is pivoted toward the sharps-releasing position, the sharps 5 acquires an amount of downward momentum. When the carrier 40 reaches the sharps-releasing position, the tubular compartment 42 comes to a relatively abrupt stop in a substantially horizontal orientation. The downward momentum of the sharps 5 forces the sharps 5 to exit the tubular compartment 42 through the slot 48. Gravity also urges the sharps 5 to exit through the slot. In the preferred embodiment, the sharps 5 rolls out through the slot under the force of gravity and continues for a short distance along the contoured ramp 50 before dropping into the interior region 20 of the container 10. The contoured ramp 50 maintains the sharps 5 in a substantially horizontal orientation for a brief duration before releasing the sharps. This provides a gradual transition between the rolling movement of the sharps before release, and the free-fall motion after release, so that the sharps remains substantially horizontal.

FIG. 6 illustrates one possible path that a syringe 5 may follow as it passes through several stages within the container 10. For purposes of illustration, the positions of the syringe 5 prior to landing are illustrated in dashed lines, and the position of the syringe after landing is illustrated in solid lines. The syringe 5 is initially placed in the carrier 40 in a substantially vertical position. After the handle 64 of the actuator 60 is depressed, the syringe 5 is pivoted to the sharps-releasing position, which is shown in a horizontal position in the illustrated embodiment, in which the sharps is held in the carrier 40 in a substantially horizontal position. When the carrier 40 reaches the sharps-releasing position, the tubular compartment 42 comes to a stop. At this moment, or at a time just prior to it, the downward momentum of the sharps 5 and/or gravitational pull on the syringe force the sharps out of the slot 48 and onto the contoured ramp 50. The contoured ramp 50 engages or supports the length of the sharps 5 and stabilizes the sharps in a substantially horizontal orientation. The sharps 5 rolls or otherwise travels on or along the ramp 50 until the point of release. After release, the sharps continues in the substantially horizontal orientation in a free-fall descent. The sharps 5 remains in the substantially horizontal orientation as it drops into the interior region 20 of the container 10. As more and more sharps are deposited, the sharps accumulate in the interior region 20 of the container 10 in a substantially parallel arrangement, as shown in FIG. 6.

Referring now to FIGS. 7-11, a sharps collection container 100 is shown in accordance with a second embodiment of the invention. The container 100 includes a cover portion 102 connected over a receptacle 118. The cover portion 102 has a top face 104 and rectangular aperture or opening 106 formed in the top face for receiving sharps. The receptacle 118 includes a hollow interior region 120 for collecting sharps that are received through the opening 106. The opening 106 has a width and length that permit insertion of sharps in an end-wise manner, where the axis of the sharps is inserted more or less normal to the top face 104 of the cover 102. The width and length of the opening 106 are preferably smaller than the length of the sharps, preventing or discouraging insertion of sharps in a lengthwise manner. In most applications, the top face 104 and opening 106 are positioned in a substantially horizontal plane, so that end-wise insertion of the sharps is done with the sharps oriented in a substantially vertical orientation. This configuration encourages users to hold sharps in a substantially vertical orientation, and more particularly to hold sharps with the pointed end facing more or less straight down, decreasing the risk of injury to the user or others who may be in the vicinity of the user.

Figure 8:
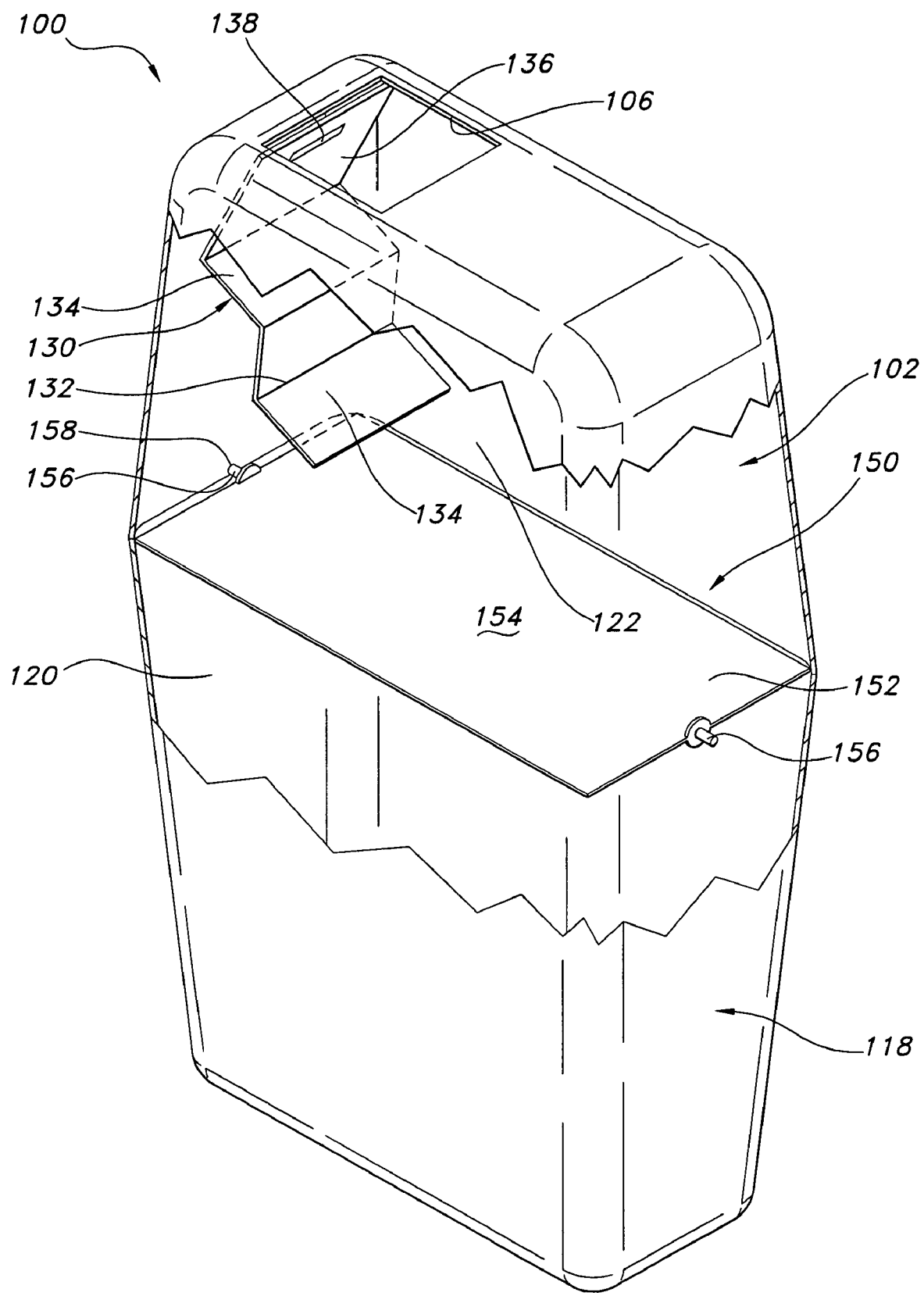
FIG. 8 is a perspective view of the sharps collection container of FIG. 7 with a portion of the container broken away to illustrate internal components in one arrangement.

As with the first embodiment, the container 100 includes one or more guide elements for reorienting sharps and guiding the sharps into a substantially parallel arrangement in the interior region 120 of the receptacle 118. Referring to FIG. 8, the container 100 includes a first guide element in the form of a ramp 130. The ramp 130 is formed from a folded sheet of light-weight, moderately rigid resilient material, such as polyethylene. Other suitable materials and forming methods are also contemplated. The sheet includes a number of folds or contours 132 that divide the sheet into a series of surfaces or panels 134.

The opening 106 is located in a position offset from the center of the top face 104 of the cover 102. With the opening 106 in this off-centered position, sharps enter into the container 100 on one side of the cover 102. The ramp 130 extends downwardly from one side of the opening 106 and projects beneath the opening. The folds 132 are arranged so that the panels 134 extend inwardly toward the center portion of the cover 102, forming a staircase-like extension that extends from the side of the cover toward the center portion of the cover. In this position, the ramp 130 acts as a deflector that intercepts sharps that drop through the opening 106. The ramp 130 redirects the sharps toward a central location in the cover, called the "rebound area" 122.

The panels 134 on ramp 130 are arranged beneath the opening 106 so that an end of the sharps lands on one or more of the panels. In the embodiment illustrated in the Figures, the light-weight, moderately rigid resilient nature of the ramp 130 optionally produces a spring-board action, where the ramp partially yields under the weight of the sharps. As the end of the sharps contacts the ramp 130, the sharps begins to topple toward the rebound area 122 and caroms off of the ramp 130 toward the rebound area. The deflection off of the ramp 130 significantly decreases the kinetic energy of the sharps.

Figure 7:
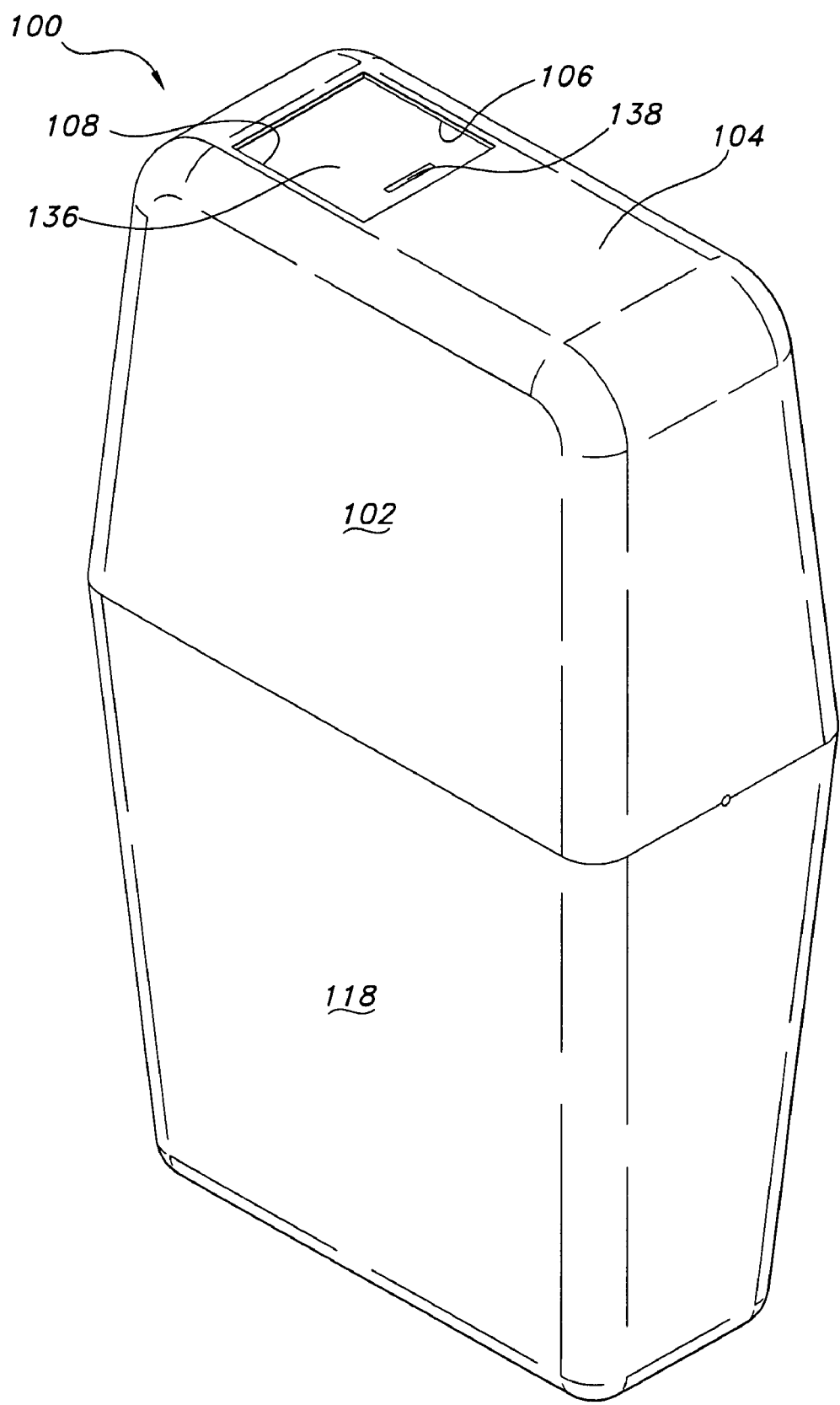
FIG. 7 is a perspective view of a sharps collection container in accordance with a second embodiment of the invention.
Figure 9:
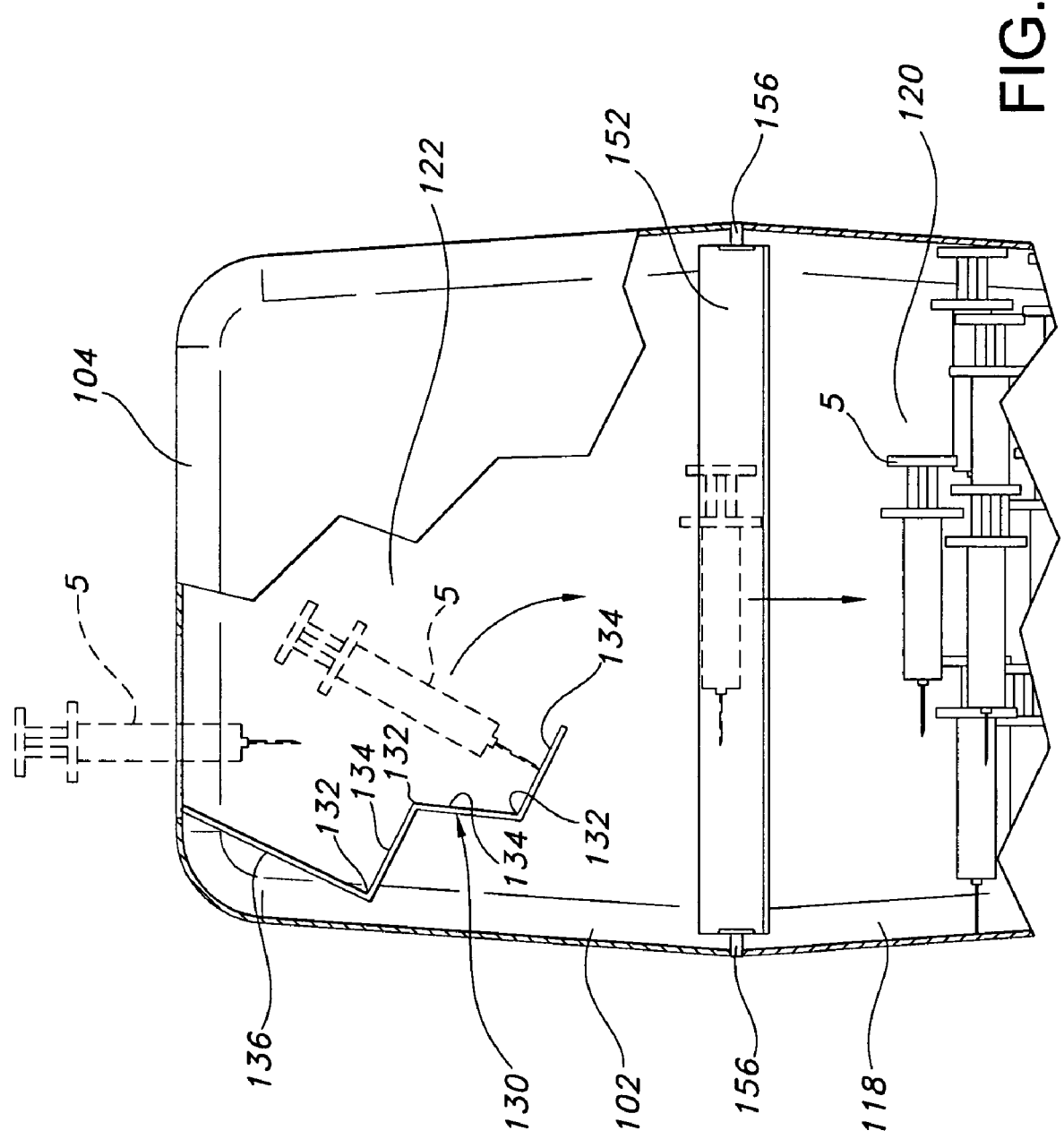
FIG. 9 is a truncated front view of the sharps collection container of FIG. 7, with a portion of the container broken away to illustrate internal components in another arrangement.
Figure 10:
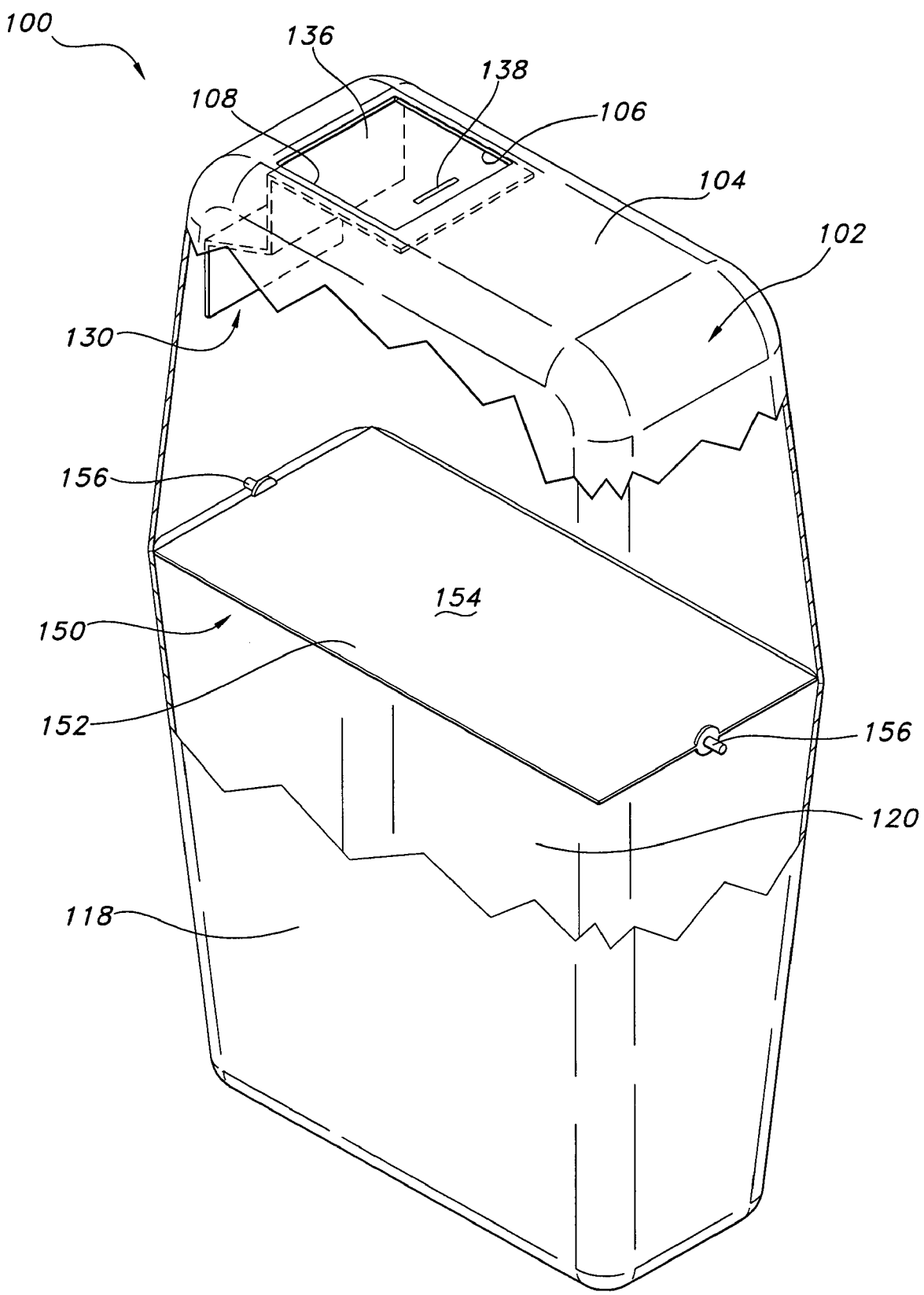
FIG. 10 is a perspective view of the sharps collection container of FIG. 7 with a portion of the container broken away to illustrate internal components in another arrangement.
Figure 11:
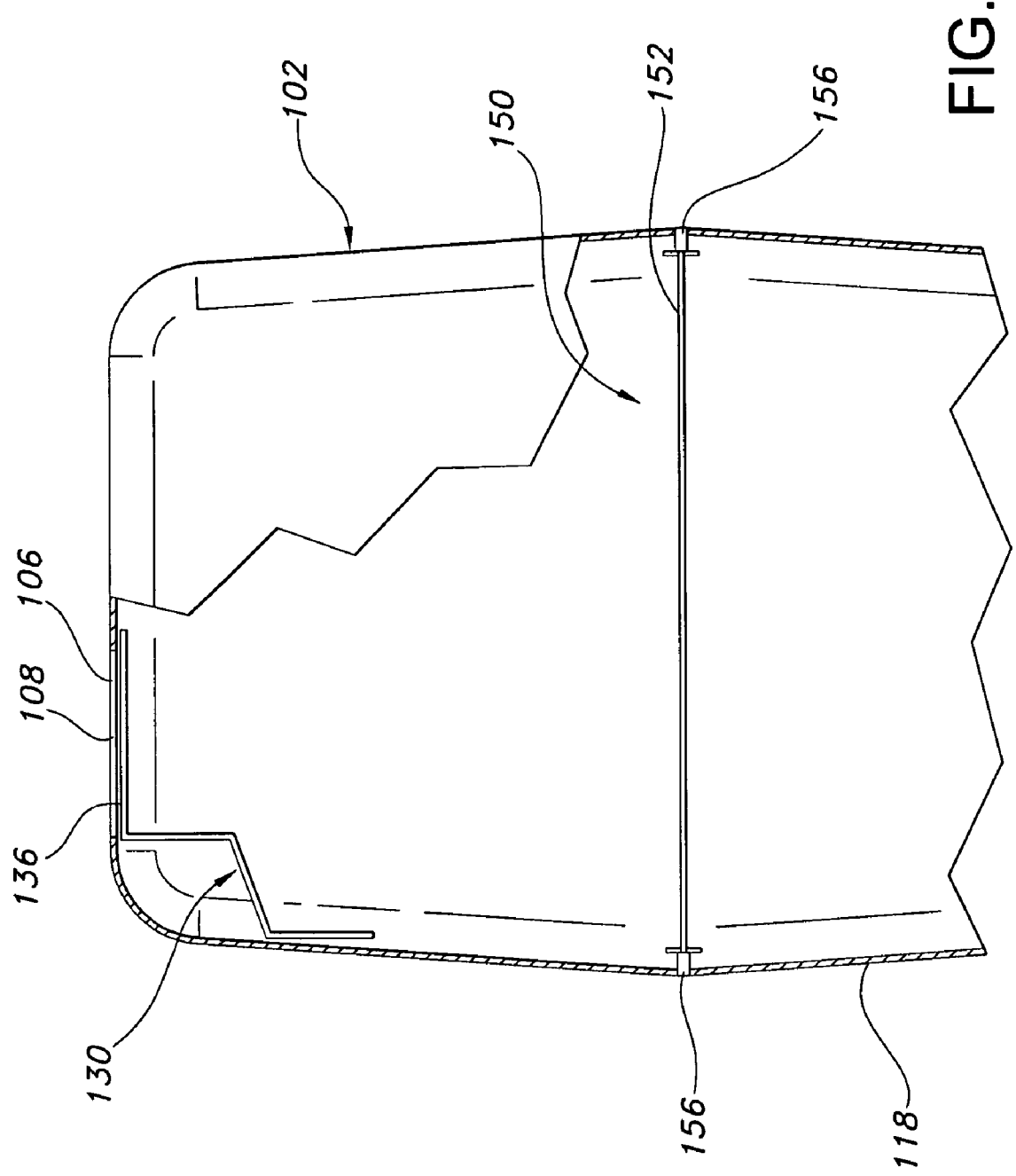
FIG. 11 is a truncated front view of the sharps collection container of FIG. 7, with a portion of the container broken away to illustrate internal components in another arrangement.
Figure 12:
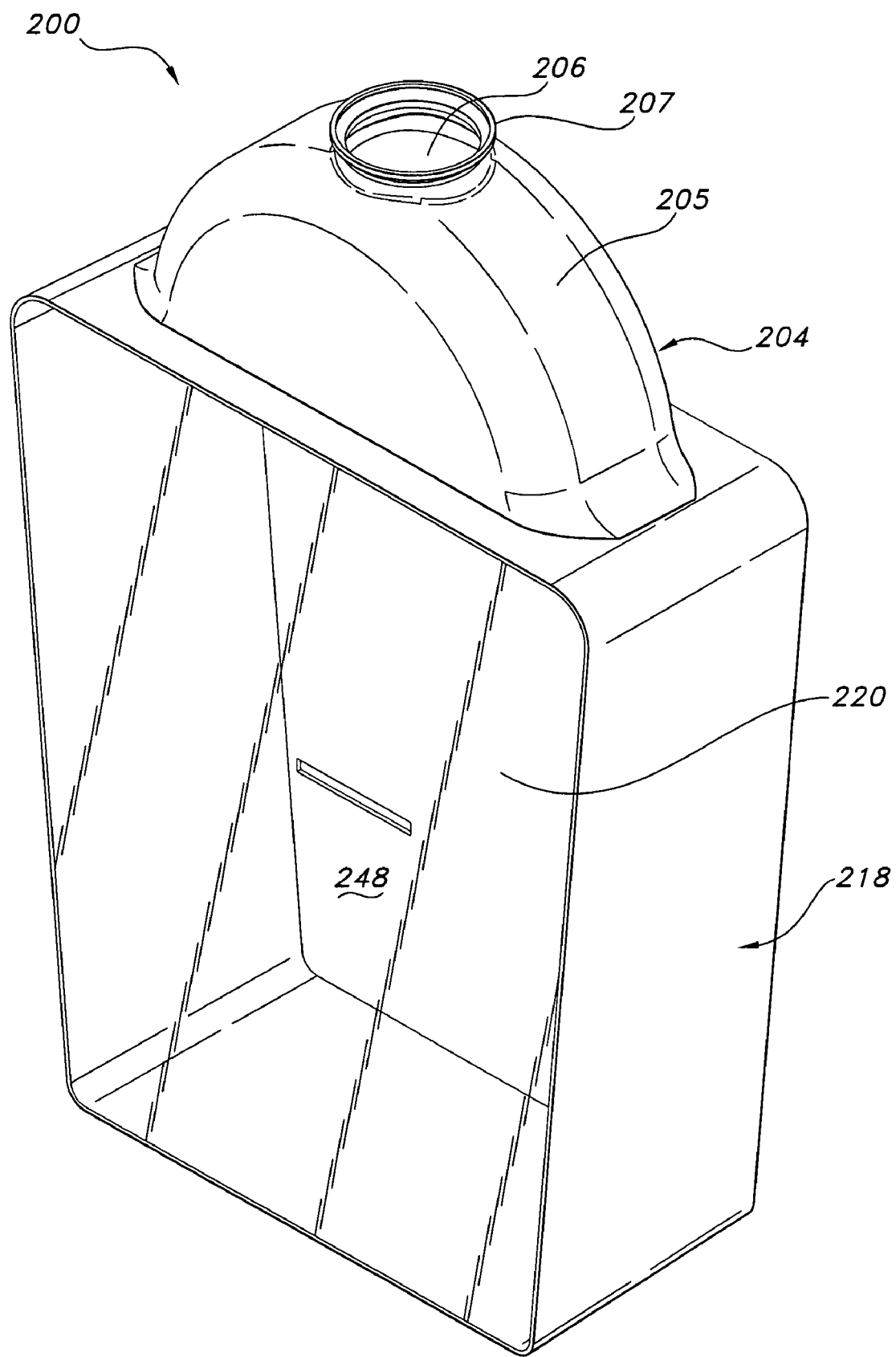
FIG. 12 is a perspective view of a sharps collection container in accordance with a third embodiment of the invention.

The top panel of the ramp 130 forms a door 136 that is slidable in the opening 106 of the cover 102. The door 136 may be connected in the opening in a variety of ways. For example, the side edges of the door 136 may include small round hubs (not shown). The corresponding sides of the opening 106 may include small tracks (not shown) having widths that are slightly larger than the diameter of the hubs. The tracks are adapted to receive the hubs and limit displacement of the door. The door is displaceable in the track between an open position, as shown in FIGS. 8 and 9, and a closed position, as shown in FIGS. 7, 10 and 11. In the open position, the door is substantially removed from the opening 106, permitting sharps to be deposited into the container in an end-wise manner through the opening. In the closed position, the door 136 occupies the opening, precluding insertion of sharps through the opening. The door 136 includes a small finger slot 138 to assist the user in sliding the door along the track in the opening between the open and closed positions.

The container 100 includes a second guide element in the form of a tumbler or platform 150 to receive sharps from the rebound area 122 after the sharps deflect off of the ramp 130. The platform 150 is substantially planar and includes a flat rectangular landing surface 154 located in a midportion of the container. The area of the landing surface 154 is slightly smaller than the cross sectional area of the midportion of the container. As a result, the platform 154 extends across substantially the entire midportion of the container when the platform is in a horizontal orientation. When the platform 154 is moved out of the horizontal position, the platform leaves a gap that forms a passage between the interior of the cover 102 and the interior region 120 of the receptacle 118. The platform 150 is movable in the container 100 between a closed position and an open position. In the closed position, the platform extends in a substantially horizontal orientation and forms a blockage between the rebound area 122 of the cover 102 and the interior region of the receptacle 118. In the open position, the platform 150 is moved out of the substantially horizontal orientation, creating a passage between the rebound area 122 and the interior region 120 of the receptacle 118.

The platform 150 may be supported in a variety of ways to facilitate the movement of the platform between the open and closed positions. Referring to FIG. 8, the platform 150 is pivotally supported in the container 100 with a pair of pivot pins 156. The pivot pins 156 extend through a pair of pivot holes 158 formed in the sidewalls of the container 100. The pivot pins 156 are preferably located at midpoints on opposite sides of the platform, in alignment with an axis extending through the center of the platform (hereinafter, the "pivot axis"). In this arrangement, the platform 150 settles in a point of balanced equilibrium in the closed position, so that the platform is biased toward the closed position under the influence of gravity. Preferably, its own center of gravity corresponds in position to the pivot axis. The platform 150 is pivotally displaceable out of the closed position in response to a loading on either side of the pivot axis. Once the loading is removed, the center of gravity of the platform 150 returns the platform to the closed position.

Thus far, the container 100 has been described and illustrated with only one platform 150. In some cases, it may be desirable to use a series of pivoting platforms in the receptacle 118, with platforms placed in a vertical arrangement. For example, a first platform may be supported at one elevation in the receptacle, and a second platform may be supported at a lower elevation in the receptacle beneath the first platform. The second platform provides an additional guide element to decrease the velocity of sharps and reorient the sharps. This may be desirable when heavier objects are dropped into the container.

Referring to FIG. 9, the operation of the container 100 will now be described. The cover 102 is placed over the receptacle 118, and the door is moved to the open position, providing access through the opening 106 into the container 100. A sharps 5 is inserted in an end-wise manner through the opening 106 in the cover 102 in a substantially vertical orientation and released into the opening. As before, the position of the sharps 5 prior to landing is illustrated in dashed lines, and the position of the sharps after landing is illustrated in solid lines.

Preferably, and in the interest of safety, the pointed end of the sharps 5 is the first end inserted through the opening. As the sharps 5 descends into the container 100, the sharps 5 travels downwardly under the influence of gravity. The pointed end of the sharps collides with one or more of the panels 134 on the ramp 130. The ramp 130 yields under the weight of the sharps 5 and impedes the downward motion of the sharps, reducing the velocity of the sharps. The resiliency in the ramp 130 propels the sharps 5 into the rebound area 122, after which the sharps drops onto the platform 150 at a significantly reduced velocity relative to the initial vertical velocity.

The platform 150 is initially at equilibrium in the closed position, with the flat surface 152 disposed in a substantially horizontal plane. After the sharps 5 is propelled into the rebound area 122, the sharps 5 free-falls in the container a short distance and subsequently lands on the platform 150. The platform 150 tilts in response to the impact force created as the sharps 5 lands on the platform or in response to the weight of the sharps 5 on the platform, moving the platform out of the horizontal plane so that one side of the platform is raised above the sharps, and one side is lowered below the sharps. The sharps 5 rolls or slides or otherwise tumbles toward the lower side of the platform 150 under the influence of gravity. As the sharps 5 moves along the surface 152, the orientation of the sharps gradually reorients into a substantially horizontal orientation. The sharps 5 then falls off the lower edge of the platform 150 and drops into the interior region 120 of the receptacle 118. As additional sharps are inserted into the container, the ramp 130 and platform 150 reorient the sharps and deliver the sharps into the interior region 120 in a substantially horizontal orientation, so that the sharps accumulate in the interior region of the receptacle in a substantially parallel and consolidated arrangement.

Referring now to FIGS. 12-16, a third embodiment of a sharps collection container 200 is shown in accordance with the present invention. The container 200 includes a top portion 204 which is molded to a receptacle 218. The top portion 204 includes a hood 205 having a generally semi-circular shape. A circular opening 206 for inserting sharps is centrally located at the top of the hood 205. The diameter of the opening 206 is larger than the maximum width of most sharps, but smaller than the length of most sharps. As with the other embodiments described above, this configuration encourages users to hold sharps in a substantially vertical orientation, and more particularly to hold sharps with the pointed end facing more or less straight down, decreasing the risk of injury to others who may be in the vicinity of the user. The opening 206 is surrounded by a circumferential rim 207 for connecting an optional cap (not shown). The receptacle 218 has an interior region 220 for collecting sharps that are inserted through the opening 206.

Figure 13:
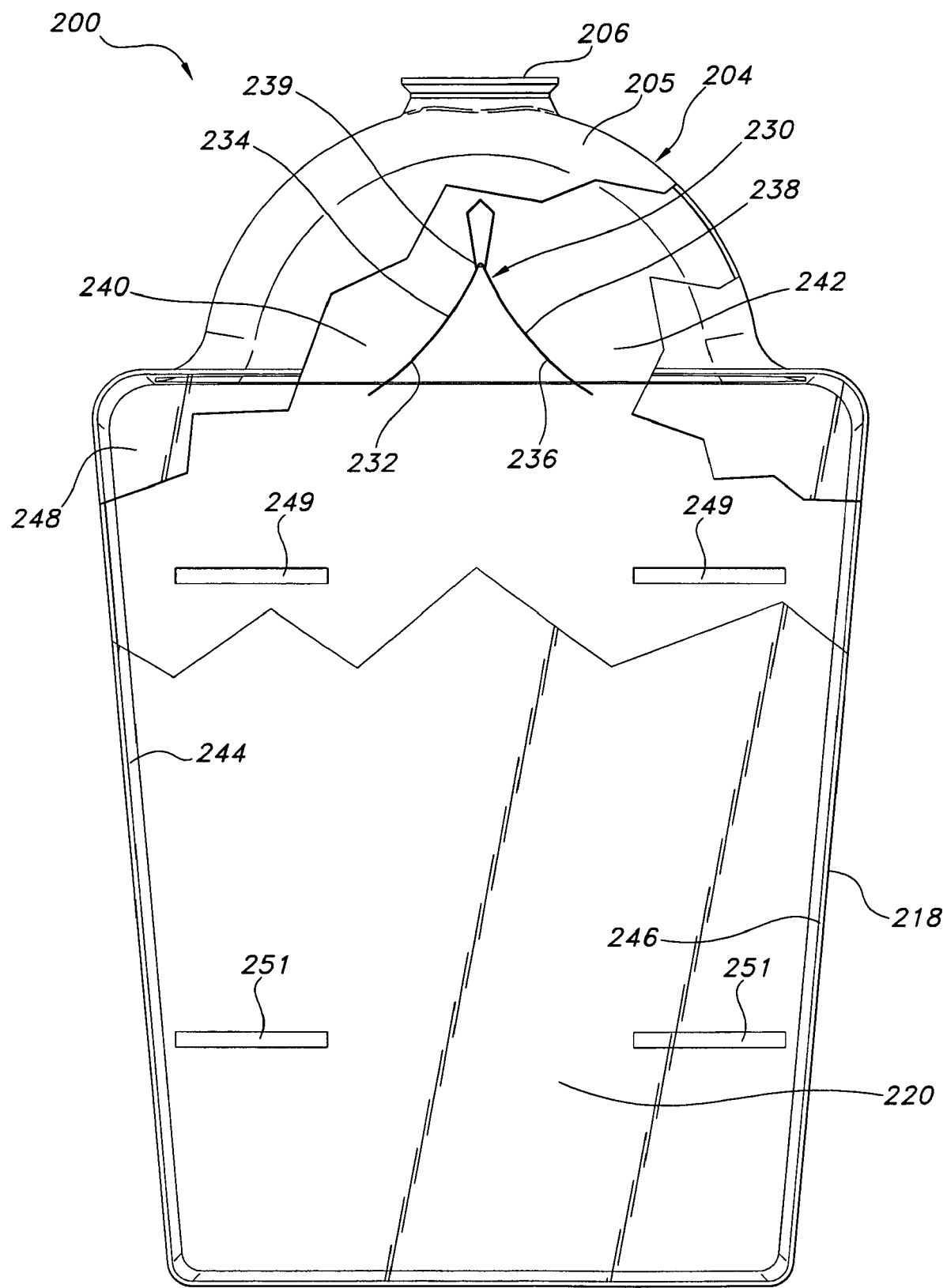
FIG. 13 is a front view of the sharps collection container of FIG. 12 with a portion of the container broken away to illustrate an internal component in one position.
Figure 14:
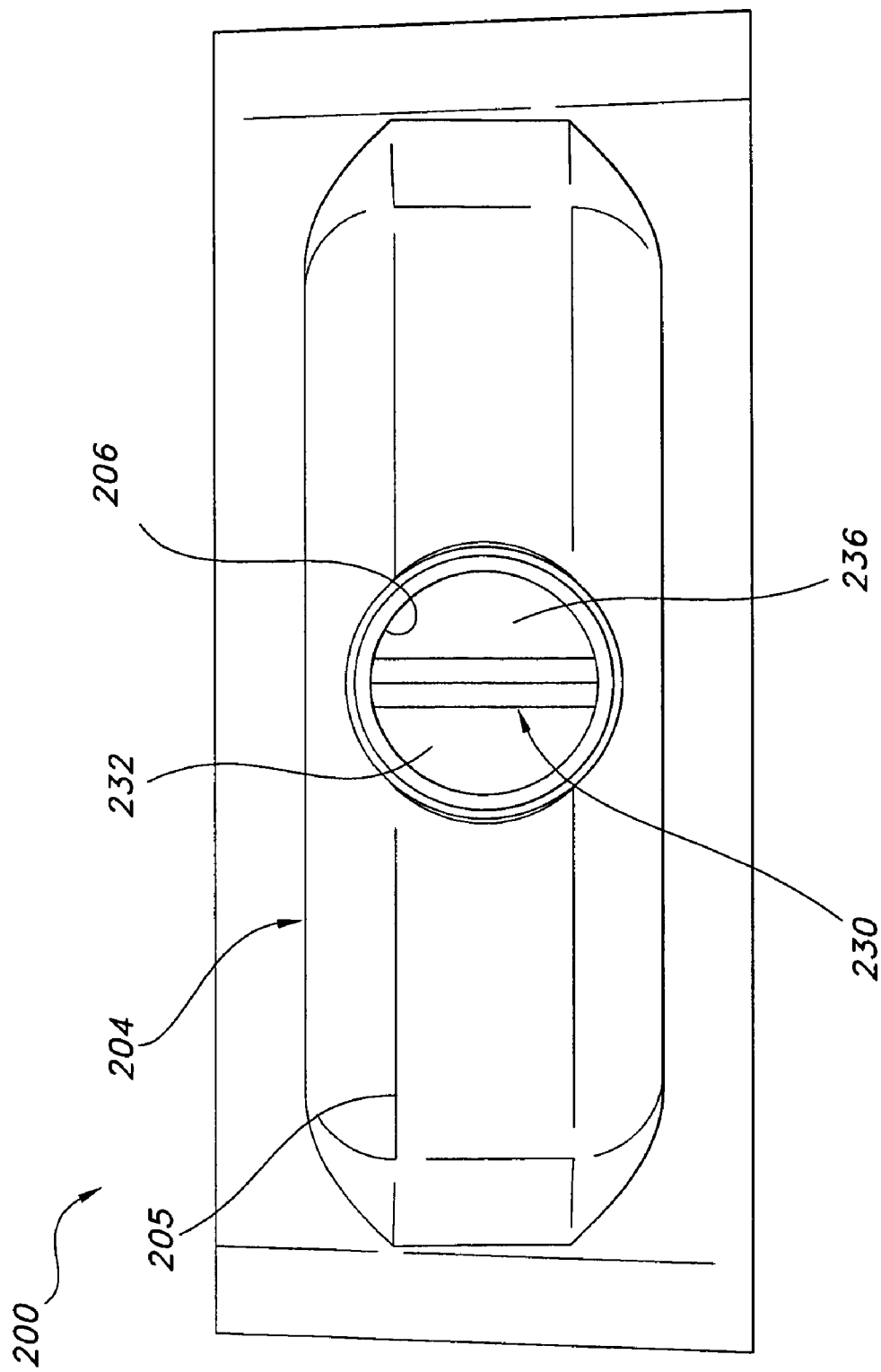
FIG. 14 is a top view of the sharps collection container of FIG. 12.

Referring to FIG. 13, the top portion 204 houses a contoured guide element in the form of a deflector 230 that is positioned beneath the opening 206. The deflector 230 includes a first ramp 232 and a second ramp 236 extending in a symmetrical arrangement with the first ramp. The first ramp 232 has a concave face 234 that extends downwardly from the opening 206, and the second ramp 236 has a concave face 238 that extends downwardly from the opening. The first ramp 232 and second ramp 234 extend outwardly in a diverging arrangement toward the side walls of the container 200. In this arrangement, the first ramp 232 forms a first drop chute 240 that directs sharps to or toward a first sidewall 244 of the container, and the second ramp 234 forms a second drop chute 242 that directs sharps to or toward a second sidewall 246 of the container which is opposite the first sidewall. The deflector 230 may be formed from a thin layer of aluminum, polyethylene, or other durable light-weight material.

Figure 15:
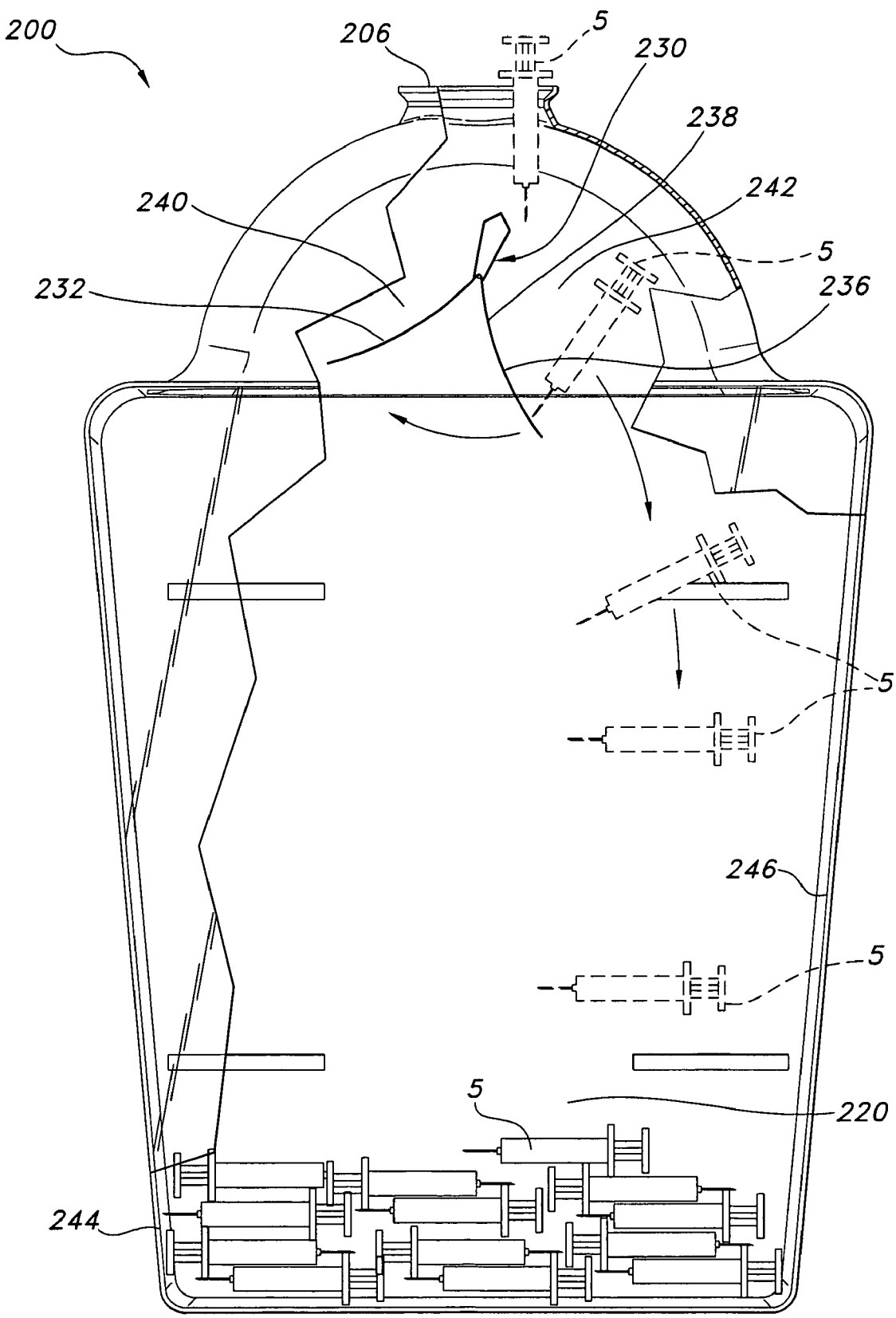
FIG. 15 is a front view of the sharps collection container of FIG. 12 with a portion of the container broken away to illustrate an internal component in another position.
Figure 16:
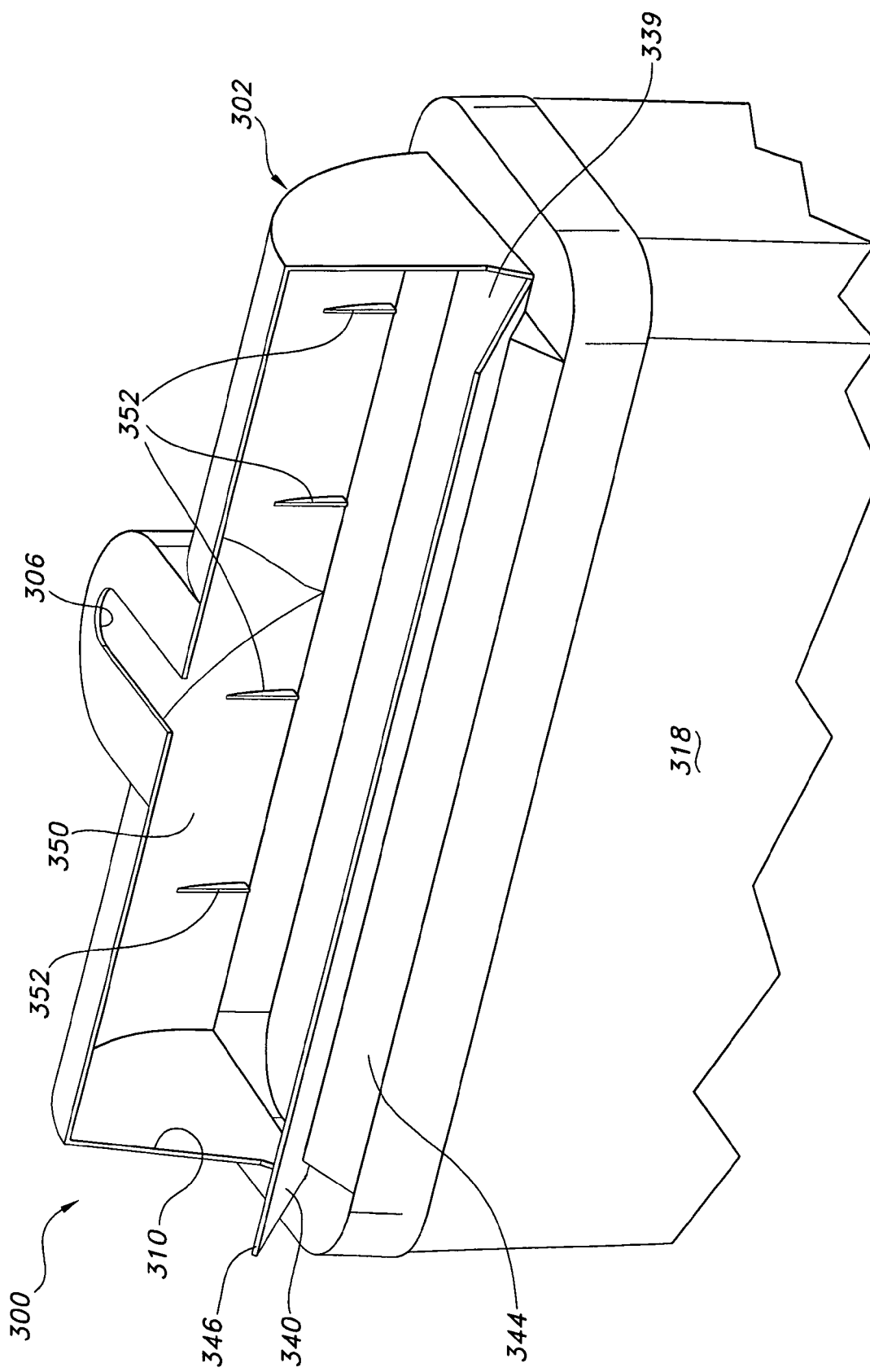
FIG. 16 is a truncated perspective view of a sharps collection container in accordance with a fourth embodiment of the invention.

The deflector 230 is pivotally mounted in the top area 204 of the container 200 by a pin 239. The pin 239 is located in a central portion of the hood 205. In the preferred embodiment, the pin 239 engages the deflector 230 at a point along the axis of symmetry between the first and second ramps 232, 236. The pin 239 preferably extends beneath the center of the circular opening 206. The deflector 230 is pivotal between a central position, as shown in FIG. 13, and a range of tilted positions, one of which is illustrated in FIG. 15.

In the central position, the deflector 230 is poised in balanced equilibrium beneath the opening 206. The first ramp 232 is positioned beneath approximately one half of the circular opening 206, and the second ramp 236 is positioned beneath the remaining half of the circular opening. In this arrangement, the first and second drop chutes 240, 242 are of substantially the same dimensions, and have a substantially equal probability of receiving sharps from the opening 206. As such, the deflector 230 is configured to vary the direction in which the pointed end of the sharps extends within the container. This may be desirable if the container is used to collect syringes having very large flanges on their ends, or other large projections that extend outwardly beyond the cross-sectional profile of the barrel. If syringes with large flanges are dropped into the receptacle with the needles oriented in the same direction, the side of the pile that receives the flanged ends will rise higher and faster than the side that receives the needle ends. As a result, the syringes will tend to accumulate in an uneven or sloped manner, forming an uneven mound of sharps that may waste space toward the top of the container. The symmetrical drop chutes 240, 242 reduce the potential for uneven mounding in the receptacle by varying the direction in which the sharps land.

The container 200 is preferably molded as a one piece container that forms a substantially permanent enclosure around sharps. When the deflector 230 is oriented in the central position, the interior of the container 200 will not be visible through the opening 206, making it difficult to assess how full the container is. Therefore, it may be desirable to incorporate one or more windows in the walls of the container 200 to permit inspection of the interior of the container. In FIG. 13, the container 200 includes a transparent wall 248 that allows visual access to the contents of the container. In addition, or as an alternative to the transparent wall 248, the container may include a non-transparent wall having one or more window slots 249. In FIG. 13, a first pair of window slots 249 are positioned adjacent to a first depth in the container 200, and a second pair of window slots 251 are positioned adjacent to a second depth in the container. Window slots, such as slots 249, 251, allow the user to monitor the level of sharps in the container 200 and determine when the container is full.

The container 200 may be molded as a one piece container that forms a substantially permanent enclosure around sharps. Alternatively, the container 200 may include a hinged door on one side that permits a bin or other receptacle to be placed inside the container for receiving sharps. For example, the transparent wall 248 may be mounted on a pair of hinges, allowing the transparent wall to act as a door. Once the bin is full, as seen through the transparent door, the door may be opened, and the bin may be carefully removed and replaced with an empty bin. The use of a bin allows the container 200 to be reused.

The container 200 may be used as a portable sharps container that may be placed on a table top or other work surface. Alternatively, the container 200 may be wall mounted with fasteners that extend through either the window slots 249, 251, or through separate keyhole slots formed in the rear wall of the container.

The operation of the sharps collection container 200 will now be described with reference to the illustration in FIG. 15. As before, A sharps 5 is inserted in an end-wise manner through the opening 206 of the container 200 in a substantially vertical orientation, and released into the opening. Preferably, and in the interest of safety, the pointed end of the sharps 5 is the first end inserted through the opening 206. As the sharps 5 descends into the container 200, the sharps 5 travels under the influence of gravity. Depending on which side of the opening 206 the sharps 5 enters, the sharps drops into either the first drop chute 240 or the second drop chute 242. In FIG. 15, the sharps 5 is inserted vertically on the right side of the opening 206 and drops into the second drop chute 244.

The deflector 230 intercepts the sharps 5 as the sharps drops through the opening 206, significantly slowing the vertical velocity of the sharps. In addition, the deflector 230 reorients the sharps. The path that the sharps 5 takes depends on a number of factors, and can be influenced by the point of entry of the sharps, the precise angle in which the sharps is held above the opening 206 before release, and other variables. FIG. 15 illustrates one possible path which the sharps may take. As before, the positions of the sharps 5 prior to landing are illustrated with dashed lines, and the position of the sharps after landing is illustrated in solid lines. As the sharps 5 descends through the opening, the pointed end of the sharps collides with the concave face 238 of the second ramp 236. In response to the impact, the deflector 230 tilts toward the first drop chute 240 and impedes the vertical velocity of the sharps. The tilting motion of the deflector 230 causes the end of the sharps 5 opposite the pointed end to topple toward the right side wall 246 of the container 200, drawing the sharps 5 out of the substantially vertical orientation. The deflector 230 continues to tilt or swing in a pendulum-like motion away from the second drop chute 242. At the same time, sharps 5 continues to tilt toward the right side wall 246 until the center of gravity of the sharps 5 pulls the sharps off of the second ramp 236. At this moment, the sharps pivots toward a more horizontal orientation and enters a free-fall. During the free fall, the sharps continues to move toward a substantially horizontal orientation. The sharps 5 drops into the interior region 220 of the receptacle 218 and settles in a substantially horizontal orientation.

As additional sharps are inserted into the container 200, the deflector 230 intercepts the sharps and sends them in a free-falling descent that gradually reorients the sharps toward a substantially horizontal orientation. Sharps that enter the container 200 through one half of the opening 206 are channeled into the first drop chute 240 and land in the receptacle 218 with the pointed ends oriented toward the second sidewall 246. Similarly, sharps that enter the container 200 through the opposite half of the opening 206 are channeled into the second drop chute 242 and land in the receptacle 218 with the pointed ends oriented toward the first sidewall 244. By varying the direction of the pointed ends of the sharps 5, the diverging set of drop chutes greatly reduces the potential for uneven mounding at the bottom of the container.

Referring now to FIGS. 16-20, a sharps collection container 300 is shown in accordance with a fourth embodiment of the invention. The container 300 includes a cover portion 302 for receiving sharps, and a receptacle 318 extending beneath the cover portion. The receptacle 318 includes a hollow interior region 320 for collecting sharps that are received through the cover portion 302. The cover 302 has an open bottom, and the receptacle 318 has an open top that aligns with the open bottom of the cover when the cover is placed over the receptacle, forming a passage or drop chute 339 between the cover and the receptacle. In this arrangement, sharps may be inserted through the cover 302 and collected inside the receptacle 318.

Unlike the embodiments described above, the cover portion 302 has multiple openings to permit sharps to be inserted into the container in different orientations. In particular, the cover portion 302 includes a vertical drop slot 306 for receiving sharps in a substantially vertical orientation, and front aperture 310 adapted to receive sharps in a substantially horizontal orientation. This arrangement offers a greater flexibility in operation by giving the user the option of inserting sharps in different orientations. In addition, the front aperture 310 allows larger objects to be dropped into the receptacle 318.

Figure 17:
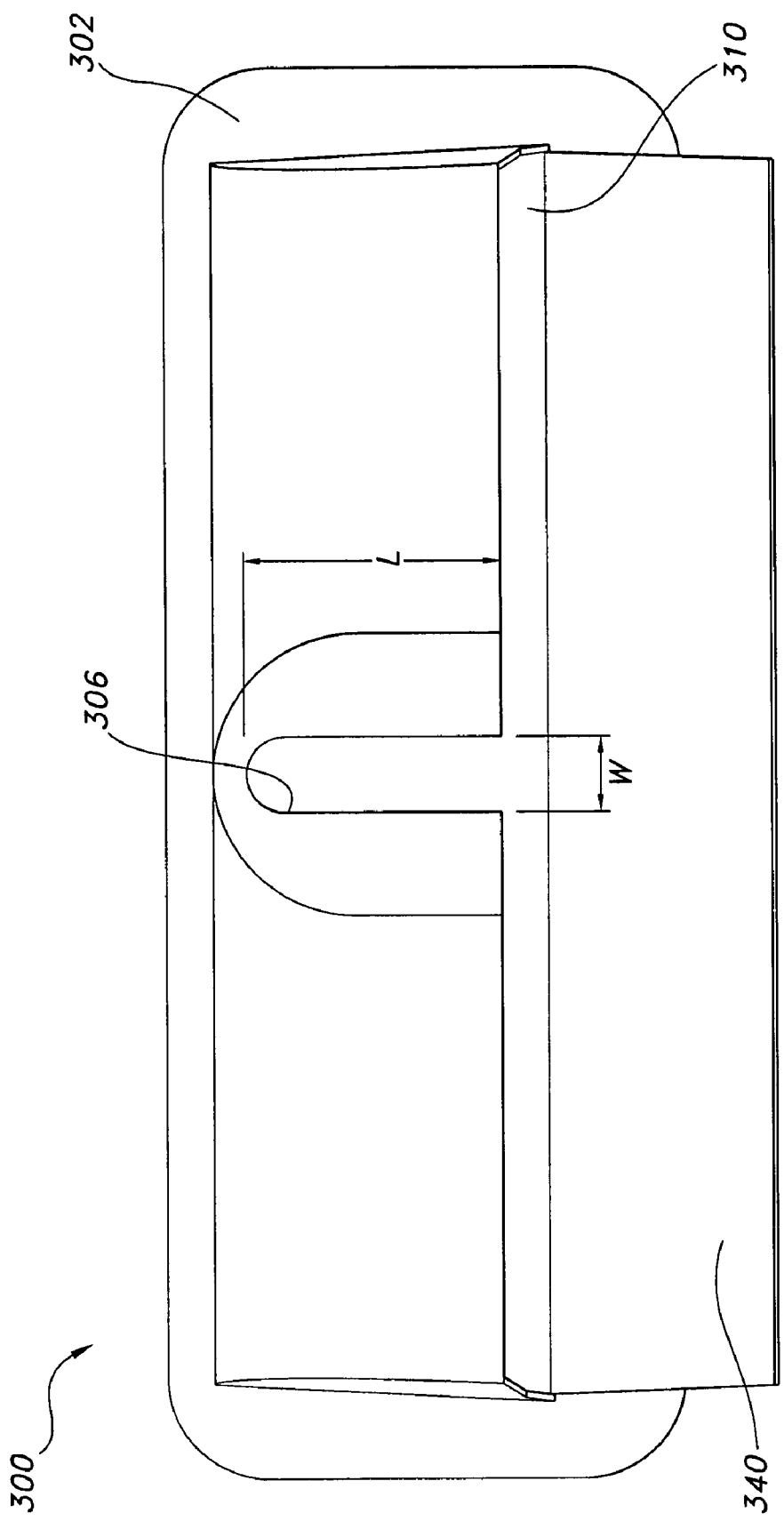
FIG. 17 is a top view of the sharps collection container of FIG. 16.

Referring to FIG. 17, the drop slot 306 has a width "W" and a length "L" that allows sharps to be inserted in a substantially vertical orientation but precludes or inhibits sharps from being inserted in a substantially horizontal orientation. More specifically, width "W" is slightly larger than the maximum width of most sharps, and length "L" is shorter than the length of most sharps. This configuration encourages users to hold sharps in a substantially vertical orientation, and more particularly to hold sharps with the pointed end facing more or less straight down, decreasing the risk of injury to others who may be in the vicinity of the user.

Figure 18:
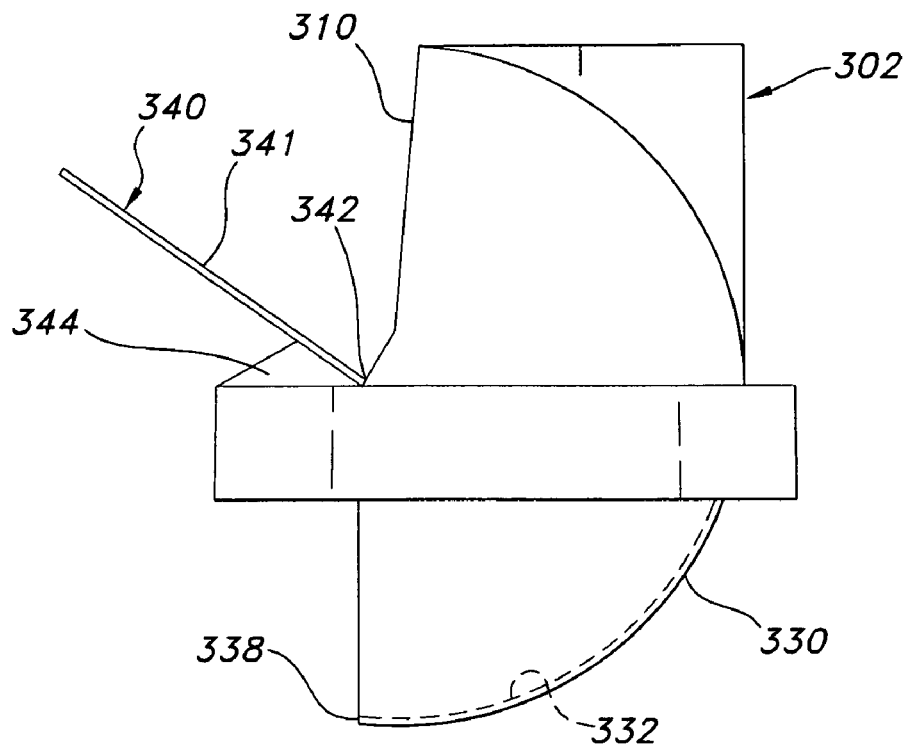
FIG. 18 is a side view of a cover on the sharps collection container of FIG. 16, showing the cover in an open condition.
Figure 19:
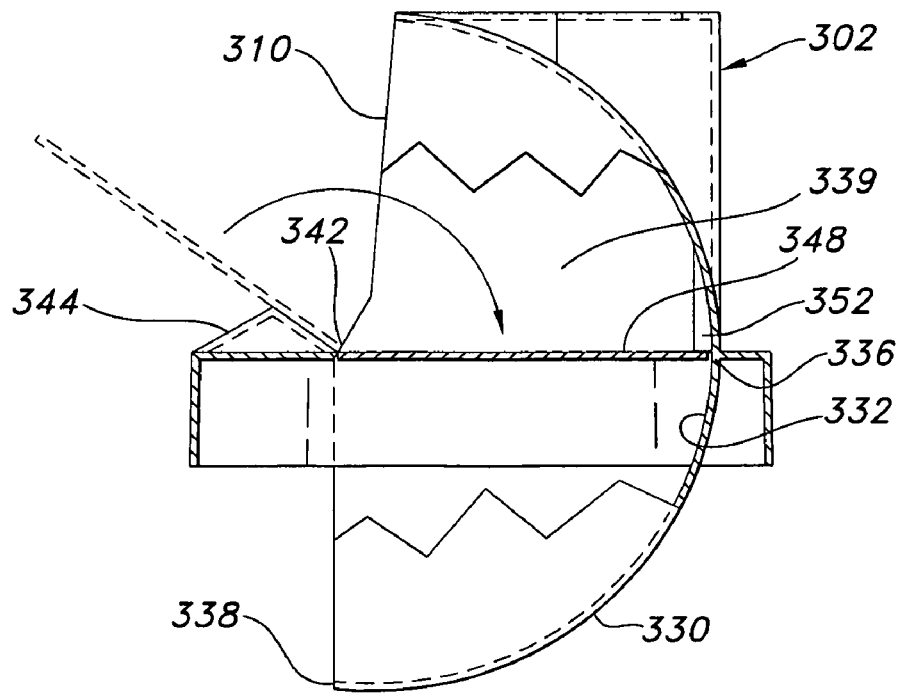
FIG. 19 is a side view of the cover on the sharps container of FIG. 16, wherein a portion is broken away to show the cover in a closed condition.

A door 340 is connected to the cover 302 along a bottom edge of the aperture 310. The door 340 is movable through the aperture 310 between an open position, as shown in FIG. 18, and a closed position, as shown in FIG. 19. In the open position, the door 340 extends upwardly and outwardly from the bottom edge of the aperture 310. The door 340 is supported on a door rest 344, which maintains the door in an inclined position that slopes downwardly toward the drop chute 339 in the container 300. In the closed position, the door 340 extends inside the cover in a substantially horizontal position, forming an obstruction between the openings 306, 310 and the drop chute 339.

The door 340 may be connected to the cover 302 in a variety of configurations that permit the door to move between the open and closed positions. For example, the door 340 may be connected to the cover 302 by a pivot connection, such as hinge 342. The hinge 342 is formed of a flexible web of material between the door 340 and the cover 302. The hinge 342 permits the door 340 to be pivoted from the open position toward the closed position, and from the closed position toward the open position. The interior of the cover 302 forms a back wall 350 having a rounded contour. The door 340 has a leading edge 346 opposite the hinge 342 that slides along or moves in proximity to the back wall 350 as the door is moved to the closed position. When the door is moved to the closed position, the door obstructs substantially all of the drop chute 339.

The container 300 preferably includes one or more components for locking the door in the closed position. Referring again to FIG. 16, the back wall 350 of the cover 302 includes a series of detents or ribs 352 that extend inwardly from the back wall toward the aperture 310. The ribs 352 are dimensioned so that they contact the leading edge 346 of the door as the door moves to the closed position. The door is resiliently flexible and bends slightly in response to the contact with the ribs 352. The degree of bend is sufficient to permit the door 340 to slide past the ribs 352 into the closed position. Referring to FIG. 19, the bottom of the ribs 352 extend over the door 340 when the door is moved past the ribs 352 into the closed position. The ribs 352 lock the door 340 in the closed position and prevent the door from being moved out of the closed position.

The container 300 includes a guide element in the form of a contoured surface that extends downwardly from the cover 302 and into the receptacle 318 when the cover is placed over the receptacle. The contoured surface may include a cantilevered extension or other structure forming a ramp. In FIGS. 18 and 19, a cowl 330 extends from the back wall 350 of the cover 302 and extends downwardly into the receptacle 318. The cowl 330 has an upper or proximal end 336 and a lower or distal end 338. The cowl 330 extends across the width and length of the container to intercept sharps that are received from the drop slot 306 and front aperture 310.

Figure 20:
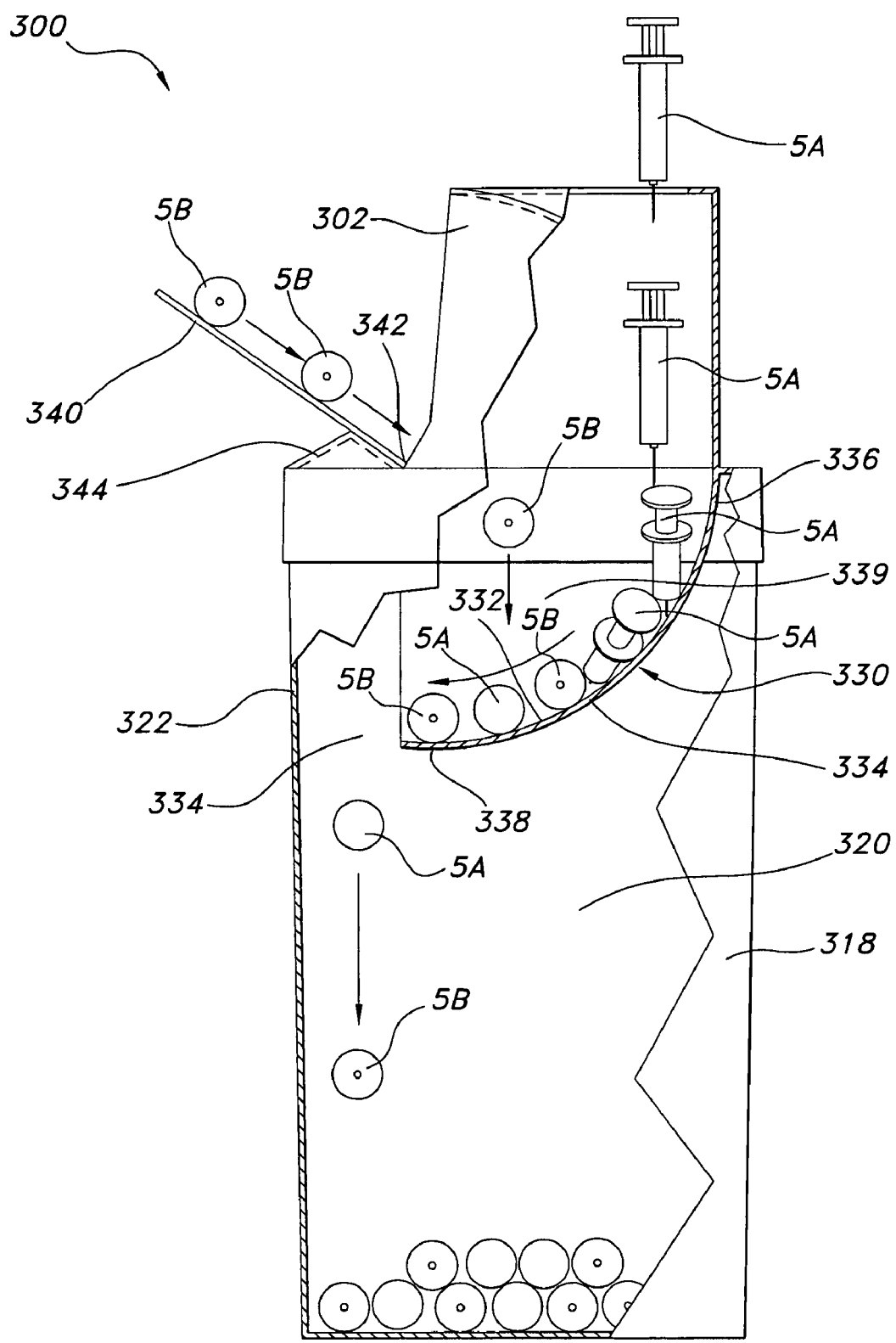
FIG. 20 is a side view of the container of FIG. 16, with a portion broken away.

Referring to FIG. 20, the cowl 330 includes a concave surface 332 that extends downwardly and toward the front wall 322 of the receptacle 318. The bottom edge 338 of the cowl 330 is spaced from the front wall 322 by a gap 334. The gap 334 forms a passageway that connects the drop chute 339 with the interior region 320 of the receptacle 318.

The manner of use of the container 300 will now be described in connection with FIG. 20. To begin, the user inserts a sharps into either the vertical drop slot 306 or the front aperture 310. For purposes of this illustration, two scenarios will be described: (1) dropping a syringe 5A into the container 300 through the vertical drop slot 306, and (2) dropping a syringe 5B into the container via the front aperture 310.

In the first scenario, the syringe 5A is held in a substantially vertical orientation, and preferably with the needle pointed downwardly toward the drop slot 306, with the barrel or plunger supported between the user's thumb and index finger. The user positions the syringe 5A in close proximity to (and preferably within) the drop slot 306, orients the syringe to a substantially vertical position directly above (and preferably within) the drop slot, and releases the barrel or plunger so that the syringe 5A drops into and through the drop slot.

In the second scenario, the syringe 5B is held above the first aperture 310. The syringe 5B is held above or on the ramp surface 341 of the door and released. After the syringe 5B is released, the syringe drops onto the ramp surface 341 and rolls or slides or tumbles downwardly until it falls into the drop chute 339.

In both scenarios, the cowl 330 redirects syringes 5A, 5B after the syringes fall into the drop chute 339. The syringes 5A, 5B descend down the concave surface 332 of the cowl 330 by rolling, sliding or a combination of rolling and sliding. The sharps 5A, 5B reach the bottom end 338 of the cowl 330 in a substantially horizontal orientation. The sharps 5A, 5B are then dropped into the interior region 320 of the container 300 in a substantially parallel arrangement.

Although the invention is illustrated and described herein with reference to specific embodiments, the invention is not intended to be limited to the particular embodiments shown. Moreover, the terms and expressions which have been employed are solely intended to be terms of description and not of limitation. There is no intention in the use of such terms and expressions of excluding any equivalents of the features shown and described or portions thereof. Various modifications may be made to the described embodiments within the scope and range of equivalents of the claims and without departing from the invention. For instance, a number of guide elements described in the different embodiments may be combined with one another or substituted for one another. The platform 150 shown in FIGS. 7-11, for example, can be incorporated into any of the containers shown in FIGS. 1, 12 and 16 as an additional guide element. The platform would serve to further decrease the vertical velocity of the sharps and orient the sharps in a substantially horizontal arrangement prior to releasing the sharps into the containers. Accordingly, the invention incorporates many variations that fall within the scope of the following claims.

What is claimed:

1. A container for collecting sharps, said container having an opening, an interior region located beneath the opening for collecting sharps received through the opening, at least one surface positioned to deflect sharps that are received through the opening, a substantially planar platform pivotally mounted beneath the opening to deflect and reorient sharps that are inserted into the opening, the substantially planar platform being settled in a point of balanced equilibrium in a substantially horizontal closed position and biased toward the closed position under the influence of gravity, and a door movable with respect to the opening between a closed position, in which the door substantially obstructs the opening, and an open position, in which the door is substantially removed from the opening, wherein the at least one surface is defined by a ramp extending downwardly from a position proximal the opening and toward the interior region of the container, the ramp being generally aligned beneath the opening to deflect and reorient sharps that are inserted into the opening, wherein the ramp is substantially removed from beneath the opening when the door is in the closed position.

2. A container for collecting sharps, the container having an opening configured and dimensioned to receive sharps in a substantially vertical orientation, an interior region located beneath the opening for collecting sharps received through the opening, at least one surface positioned to deflect sharps that are received through the opening to reposition the sharps from the substantially vertical orientation into a substantially horizontal orientation, and a substantially planar platform pivotally mounted beneath the opening to deflect and reorient sharps that are inserted into the opening such that the sharps are positioned substantially parallel to one another within the interior region of the container, the substantially planar platform being settled in a point of balanced equilibrium in a substantially horizontal closed position and biased toward the closed position under the influence of gravity.

3. The container of claim 2, wherein the at least one surface is defined by a ramp extending downwardly from a position proximal the opening and toward the interior region of the container, the ramp being generally aligned beneath the opening to deflect and reorient sharps that are inserted into the opening.

4. The container of claim 3 comprising a door, the door being movable with respect to the opening between a closed position, in which the door substantially obstructs the opening, and an open position, in which the door is substantially removed from the opening.

5. The container of claim 4, the door being slidably displaceable with respect to the opening between the closed and open positions.

6. The container of claim 4, the door and the ramp being movable in unison, wherein the ramp is generally aligned beneath the opening when the door is in the open position.

7. The container of claim 3, wherein the door and the ramp are integrally connected.

8. The container of claim 2 comprising a door, the door being movable with respect to the opening between a closed position, in which the door substantially obstructs the opening, and an open position, in which the door is substantially removed from the opening.

9. The container of claim 2 wherein the at least one surface is resilient such that the at least one surface partially yields under the weight of the sharps.

10. The container of claim 2 wherein the at least one surface has contours dividing the at least one surface into panels.

11. The container of claim 10 wherein the contours form a staircase-like extension.

12. The container of claim 2 wherein the at least one surface decreases the kinetic energy of the sharps.

13. A container for collecting sharps comprising:
a receptacle including a storage area configured and dimensioned to receive the sharps, the receptacle having a length, a width, and a height;
a cover portion releasably connected to the receptacle and including an opening configured and dimensioned to receive the sharps in a substantially vertical orientation;
at least one ramp positioned beneath the opening in the cover portion, the at least one ramp being configured and dimensioned for engagement with an end of the sharps following passage through the opening in the cover portion to reposition the sharps from the substantially vertical orientation into a substantially horizontal orientation; and
a platform mounted within the receptacle for movement between a first position, wherein the platform inhibits continued passage of the sharps through the container, and a second position, wherein the platform allows for continued passage of the sharps such that the sharps are positioned substantially parallel to one another within the storage area of the receptacle.

14. The container of claim 13, wherein the cover portion defines an interior region located beneath the opening for collecting sharps received through the opening.

15. The container of claim 14, wherein the at least one ramp is configured and dimensioned for movement through the interior region of the cover portion along a longitudinal axis of the container.

16. The container of claim 14, wherein the at least one ramp includes a plurality of panels connected to define a staircase-like extension extending into the interior region of the cover portion to reduce kinetic energy of the sharps during movement of the sharps through the interior region of the cover portion.

17. The container of claim 13, wherein the platform is biased towards the first position.

18. The container of claim 17, wherein the platform is configured and dimensioned such that engagement of the sharps with the platform moves the platform from the first position to the second position.

19. The container of claim 13, wherein the platform is configured and dimensioned for pivotal movement between the first position and the second position.

20. The container of claim 19, wherein the platform includes pivot pins configured and dimensioned for positioning within pivot holes formed in sidewalls of the container.

21. The container of claim 20, wherein the pivot pins are located substantially adjacent a midpoint of the platform such that the platform is settled in a point of balanced equilibrium in the first position.

22. The container of claim 13, wherein the cover portion further comprises a door movable relative to the opening in the cover portion, the door being movable between a closed position, wherein the door substantially obstructs the opening in the cover portion, and an open position, wherein the door is substantially removed from the opening in the cover portion.

23. The container of claim 22, wherein the door is configured and dimensioned for sliding movement between the closed position and the open position.

24. A container for collecting sharps comprising:
a receptacle configured and dimensioned to receive sharps, the receptacle having a length, a width, and a height;
a cover portion releasably connected to the receptacle, the cover portion including an opening configured and dimensioned to receive the sharps in a substantially vertical orientation corresponding to the height of the receptacle, the cover portion including an interior region positioned beneath the opening configured and dimensioned to collect sharps received through the opening; and
means for reorienting the sharps from the substantially vertical orientation to a substantially horizontal orientation, the sharps being positioned substantially along the length of the receptacle in the horizontal position, wherein the means for reorienting the sharps includes:
at least one ramp movable through the interior region of the cover portion; and
a platform pivotally mounted within the receptacle such that the platform is movable between an open position, wherein the platform defines a gap with an interior wall of the receptacle configured and dimensioned to permit passage of the sharps, and a closed position, wherein the platform and the interior wall of the receptacle collectively inhibit passage of the sharps.

* * * * *